(12) United States Patent
Portal

(10) Patent No.: US 8,513,307 B2
(45) Date of Patent: Aug. 20, 2013

(54) N-PHENYLACETAMIDE INHIBITORS OF THE ENZYME SOAT-1 AND PHARMACEUTICAL/COSMETIC COMPOSITIONS COMPRISED THEREOF

(75) Inventor: Thibaud Portal, Opio (FR)

(73) Assignee: Galderma Research & Development, Biot (FR)

( * ) Notice: Subject to any disclaimer, the term of this patent is extended or adjusted under 35 U.S.C. 154(b) by 491 days.

(21) Appl. No.: 12/717,998

(22) Filed: Mar. 5, 2010

(65) Prior Publication Data

US 2010/0273813 A1    Oct. 28, 2010

Related U.S. Application Data

(63) Continuation of application No. PCT/EP2008/061777, filed on Sep. 5, 2008.

(60) Provisional application No. 60/960,096, filed on Sep. 14, 2007.

(30) Foreign Application Priority Data

Sep. 6, 2007 (FR) ...................... 07 57393

(51) Int. Cl.
*A01N 37/18* (2006.01)
*A61K 31/16* (2006.01)
*A61K 8/02* (2006.01)
*C07C 233/00* (2006.01)
*C07C 235/00* (2006.01)
*C07C 237/00* (2006.01)
*C07C 239/00* (2006.01)

(52) U.S. Cl.
USPC ............... 514/613; 564/123; 424/401

(58) Field of Classification Search
USPC .................. 514/613; 564/123; 424/401
See application file for complete search history.

(56) References Cited

FOREIGN PATENT DOCUMENTS
EP    0987254 B1    3/2000
EP    1431294 A1    6/2004

OTHER PUBLICATIONS

Vippagunta et. al., Advanced Drug Delivery Reviews, 2001, Elsevier, vol. 48, pp. 3-26.*
International Search Report corresponding to PCT/EP 2008/061777 dated Oct. 29, 2008.

* cited by examiner

*Primary Examiner* — Sreeni Padmanabhan
*Assistant Examiner* — Sarah Pihonak
(74) *Attorney, Agent, or Firm* — Dentons US LLP

(57) ABSTRACT

Novel N-phenylacetamide compounds of formula (I):

(I)

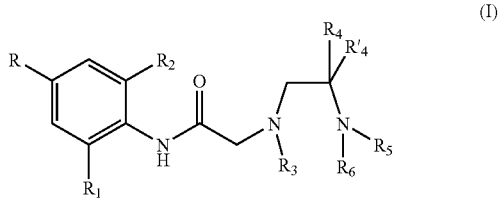

and cosmetic and pharmaceutical compositions containing same are useful for treating disorders of the sebaceous gland, e.g., acne, or have cosmetic applications.

25 Claims, No Drawings

N-PHENYLACETAMIDE INHIBITORS OF THE ENZYME SOAT-1 AND PHARMACEUTICAL/COSMETIC COMPOSITIONS COMPRISED THEREOF

CROSS-REFERENCE TO ALL PRIOR APPLICATIONS

This application is a continuation of PCT/EP 2008/061777, filed Sep. 5, 2008 and designating the United States (published in the English language on Mar. 12, 2009 as WO 2009/030750 A1), which claims benefit of U.S. Provisional Application No. 60/960,096, filed Sep. 14, 2007, and also claims priority of FR 0757393, filed Sep. 6, 2007, each hereby expressly incorporated by reference in its entirety and each assigned to the assignee hereof.

BACKGROUND OF THE INVENTION

1. Technical Field of the Invention

The present invention relates to novel N-phenylacetamide compound inhibitors of the enzyme SOAT-1 (Sterol-O-Acyl Transferase-1), likewise named ACAT-1 (Acylcoenzyme A Cholesterol Acyl Transferase). It also relates to their formulation into pharmaceutical compositions useful in human or veterinary medicine, or else into cosmetic compositions and also their non-therapeutic applications.

2. Description of Background and/or Related and/or Prior Art

The compounds having an inhibitory activity on SOAT-1 are widely described in the literature as having activities in the regulation of biological processes involving cholesterol and its derivatives. These properties confer on this class of compounds a great potential in the treatment or the prevention of numerous pathologies, and more particularly in dermatology and in cardiovascular diseases or complaints of the central nervous system. The majority of the biological effects of the inhibitors of SOAT-1 are mediated by the prevention of the synthesis of esters of cholesterol by the enzyme SOAT-1. Among the documents of the prior art describing inhibitory molecules of SOAT-1, exemplary are WO 96/10559, EP-0370740, EP-0424194, U.S. Pat. No. 4,623,663, EP-0557171, U.S. Pat. No. 5,003,106, EP-0293880, EP-0433662 and U.S. Pat. No. 5,106,873, which describe compounds for treating arteriosclerosis or hypercholesterolaemia to be treated. The therapeutic potential of inhibitors of SOAT-1 in the treatment of cardiovascular diseases and, in particular, of hypercholesterolaemia and of arteriosclerosis is likewise described by Kharbanda R. K. et al., in *Circulation*, 2005, 11, 804. The potential of inhibitors of SOAT-1 for the treatment of Alzheimer's disease has likewise been reported in the literature, for example, by Puglielli, L. et al., in *Nature Neurosciences* 2003, 6 (4), 345.

U.S. Pat. Nos. 6,133,326, 6,271,268 and WO 2005/034931 themselves describe compounds which are inhibitors of SOAT-1 for inhibiting the production of sebum. In the field of dermatology in particular, it is particularly advantageous to prevent the excessive production of sebum and all the associated conditions.

Sebum is produced by the sebaceous gland. The greatest concentration of sebaceous glands is situated on the face, the shoulders, the back and the scalp. The sebum is secreted on the surface of the skin, where it plays a major physiological role, associated with the maintenance of the cutaneous barrier and of a microenvironment allowing the regulation of the bacterial flora and cutaneous fungus.

The hyperproduction of sebum is, most often, associated with a skin or a scalp of greasy appearance, a cause of discomfort and a degraded appearance. In addition, the hyperproduction of sebum can breed seborrhoeic dermatitis and is associated with an increased incidence or severity of acne. The esters of cholesterol produced in the sebaceous gland by SOAT-1 are one of the components of sebum, amongst several classes of lipids including the triglycerides, the esters of waxes and the squalenes, as described by Nikkari, T., in *J Invest Derm.*, 1974, 62, 257. The inhibition of this enzyme or other acyltransferases can thus allow the production of sebum to be inhibited. U.S. Pat. No. 6,133,326 describes, in particular, the inhibition of the sebum by inhibitors of ACAT-1 (likewise named SOAT-1). Nevertheless, to date, no treatment utilizing such inhibitors is available commercially. The only treatments allowing the disorders linked to hyperseborrhoea to be remedied are systemic hormonal treatments or systemic treatment with 13-cis-retinoic acid, treatments whose secondary effects considerably limit of their field of application. There thus exists a clear cosmetic and medical need for the treatment of disorders and pathologies linked to the hyperproduction of sebum.

SUMMARY OF THE INVENTION

The present invention features novel N-phenylacetamide compounds which are potent inhibitors of the enzyme SOAT-1.

Thus, this invention features novel N-phenylacetamide compound inhibitors of the enzyme SOAT-1, having the following general formula (I):

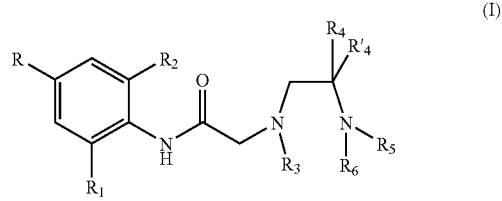

in which:

R is a hydrogen atom, a $(C_1-C_6)$alkyl radical, a —$CH_2$—$NR_aR_b$ radical, a —$C(O)$—$NR_aR_b$ radical or a —$C(S)$—$NR_aR_b$ radical, wherein $R_a$ is a hydrogen atom or a $(C_1-C_4)$ alkyl radical and $R_b$ is a hydrogen atom, a phenyl or a cycloalkyl radical, $R_1$ is a $(C_1-C_6)$alkyl radical, $R_2$ is a hydrogen, chlorine, fluorine or bromine atom, or a $(C_1-C_6)$alkyl radical, $R_3$ is a hydrogen atom or a radical —$C(O)R_7$ wherein $R_7$ is a $(C_1-C_6)$alkyl or $(C_1-C_6)$alkoxy radical, or else $R_3$ is bonded to $R_6$ and —$R_3$-$R_6$— is —$C(O)$—, —$C(O)CH_2$—, —$SO_2$— or —$CH_2$—, $R_4$ and $R'_4$ are identical and are each a $(C_1-C_6)$alkyl radical or else, $R_4$ and $R'_4$ are bonded to one another and form, together with the carbon atom from which they depend, a cycloalkyl group, $R_5$ is a group selected from among:

(i) an unsubstituted phenyl radical or a phenyl radical substituted by one to three identical or different substituents selected from among the atoms fluorine, chlorine, iodine or bromine, or the radicals $(C_1-C_6)$alkyl, hydroxymethyl, mono-, di- or trifluoromethyl, hydroxyl, phenyl, 2-pyridyl, 3-pyridyl or 4-pyridyl, $(C_1-C_6)$alkoxy, phenoxy, benzyloxy, mono-, di- or trifluoromethoxy, (ii) a $(C_1-C_{12})$alkyl radical, optionally substituted by one or more hydroxyl groups, fluorine, chlorine, iodine or bromine atoms, (iii) a cycloalkyl radical or a —$(CH_2)_m$-cycloalkyl radical in which m is equal to 1, 2 or 3, (iv) an aralkyl radical —$(CH_2)_n$—Ar with n equal to 1, 2 or 3 and Ar is an unsubstituted phenyl radical, unsubstituted naphthyl, or a phenyl radical substituted by one to three identical or different substituents selected from among the atoms fluorine, chlorine, iodine or bromine, or the radicals $(C_1-C_6)$alkyl, hydroxymethyl, mono-, di- or trifluoromethyl, hydroxyl, phenyl, 2-pyridyl, 3-pyridyl or 4-pyridyl, $(C_1-C_6)$ alkoxy, phenoxy, benzyloxy, mono-, di- or trifluoromethoxy, with the proviso that when $R_3$ is bonded to $R_6$ and —$R_3$-$R_6$— is —$C(O)CH_2$—, then $R_5$ is different from a benzyl radical or a group comprising from 4 to 12 carbon atoms of formula —$CH_2$—$CH(OH)$—$(CH_2)_p$-alkyl in which p is an integer of from 1 and 9, and the alkyl radical can optionally be substituted by one or more hydroxyl groups, or fluorine, chlorine, iodine or bromine atoms, $R_6$ is a hydrogen atom or else $R_6$ is bonded to $R_3$ and —$R_3$-$R_6$— is —$C(O)$—, —$C(O)CH_2$—, —$SO_2$— or —$CH_2$—, as well as their pharmaceutically acceptable salts, solvates or hydrates and their conformers or rotamers.

In the definition of the compounds of formula (I) above, when $R_3$ is bonded to $R_6$ and —$R_3$-$R_6$— is —$C(O)CH_2$—, then $R_5$ is, preferably, an unsubstituted phenyl radical or a phenyl radical substituted by one to three identical or different substituents selected from among the atoms fluorine, chlorine, iodine or bromine, or the radicals $(C_1-C_6)$alkyl, hydroxymethyl, mono-, di- or trifluoromethyl, hydroxyl, phenyl, 2-pyridyl, 3-pyridyl or 4-pyridyl, $(C_1-C_6)$alkoxy, phenoxy, benzyloxy, mono-, di- or trifluoromethoxy.

"Alkyl radical" means a saturated, linear or branched hydrocarbon chain. "$(C_1-C_{12})$alkyl" means an alkyl chain comprising from 1 to 12 carbon atoms. "$(C_1-C_6)$alkyl" means an alkyl chain comprising from 1 to 6 carbon atoms. Exemplary of $(C_1-C_6)$alkyl are methyl, ethyl, n-propyl, isopropyl, n-butyl, tert-butyl, sec-butyl, pentyl and hexyl radicals.

"$(C_1-C_4)$alkyl" means an alkyl chain comprising from 1 to 4 carbon atoms. Exemplary of $(C_1-C_4)$alkyl are methyl, ethyl, n-propyl, isopropyl, n-butyl, tert-butyl and sec-butyl radicals.

"$(C_1-C_6)$alkoxy" designates an —O—$(C_1-C_6)$alkyl radical. Likewise, $(C_1-C_4)$alkoxy designates an —O—$(C_1-C_4)$ alkyl radical.

Phenoxy designates an —O-phenyl radical.

"Cycloalkyl group" designates a cyclic, saturated hydrocarbon chain, comprising from 3 to 7 carbon atoms. Exemplary of a cycloalkyl group are cyclopropyl, cyclobutyl, cyclopentyl, cyclohexyl and cycloheptyl radicals.

DETAILED DESCRIPTION OF BEST MODE AND SPECIFIC/PREFERRED EMBODIMENTS OF THE INVENTION

Preferred compounds of formula (I) defined above are those in which:

R is a hydrogen atom, $R_1$ is a $(C_1-C_4)$alkyl radical, $R_2$ is a hydrogen, fluorine, chlorine or bromine atom or a $(C_1-C_4)$alkyl radical, $R_3$ is a hydrogen atom or a —$C(O)R_7$ radical wherein $R_7$ is a $(C_1-C_4)$alkyl or $(C_1-C_4)$alkoxy radical, or else $R_3$ is bonded to $R_6$ and —$R_3$-$R_6$— is —$C(O)$—, —$C(O)CH_2$—, —$SO_2$—or —$CH_2$, $R_4$ and $R'_4$ are identical and are each a $(C_1-C_4)$alkyl radical or else, $R_4$ and $R'_4$ are bonded to one another and together form, with the carbon atom from which they depend, a cycloalkyl group having 5, 6 or 7 carbon atoms, $R_5$ is a group selected from among:

(i) an unsubstituted phenyl radical or phenyl substituted by one, two or three identical or different substituents selected from among the atoms fluorine, chlorine and bromine, or the radicals $(C_1-C_4)$alkyl, trifluoromethyl, hydroxymethyl, mono-, di- and trifluoromethoxy, $(C_1-C_4)$alkoxy, phenoxy, benzyloxy, phenyl, 2-pyridyl, 3-pyridyl and 4-pyridyl, (ii) a $(C_2-C_{12})$alkyl radical, optionally substituted by one or more hydroxyl groups or fluorine atoms, (iii) a cycloalkyl radical or a —$CH_2$-cycloalkyl radical, (iv) an aralkyl radical —$(CH_2)_n$—Ar in which n is equal to 1, 2 or 3 and Ar is an unsubstituted phenyl radical or phenyl monosubstituted by a $(C_1-C_4)$alkyl, trifluoromethyl or $(C_1-C_4)$alkoxy radical, or a fluorine, chlorine or bromine atom, with the proviso that when $R_3$ is bonded to $R_6$ and —$R_3$-$R_6$— is —$C(O)CH_2$—, then $R_5$ is different from a benzyl radical or a radical comprising from 4 to 12 carbon atoms of formula —$CH_2$—$CH(OH)$—$(CH_2)_p$-alkyl in which p is an integer of from 1 and 9, and the alkyl radical can optionally be substituted by one or more hydroxyl groups or fluorine atoms, $R_6$ is a hydrogen atom or else $R_6$ is bonded to $R_3$ and —$R_3$-$R_6$— is —$C(O)$—, —$C(O)CH_2$—, —$SO_2$— or —$CH_2$—, as well as their pharmaceutically acceptable salts, solvates or hydrates and their conformers or rotamers.

According to the present invention, amongst the compounds of formula (I) such as defined above, particularly preferred compounds are those which have one or a combination of the following characteristics:

R is a hydrogen atom, $R_1$ is a methyl, ethyl or isopropyl radical, $R_2$ is an ethyl, isopropyl or tert-butyl radical, $R_3$ is a hydrogen atom or a radical —$C(O)R_7$ wherein $R_7$ is a methyl radical, or tert-butoxy radical, or else $R_3$ is bonded to $R_6$ and —$R_3$-$R_6$— is —$C(O)$—, —$C(O)CH_2$—, —$SO_2$— or —$CH_2$—, $R_4$ and $R'_4$ are identical and are each an ethyl or n-propyl radical, or else $R_4$ and $R'_4$ are bonded to one another and together form, with the carbon atom from which they depend, a cyclopentyl or cyclohexyl group, $R_5$ is a group selected from among:

(i) a phenyl radical or phenyl monosubstituted, preferably in the meta or para position, by a methyl, ethyl, n-butyl or benzyloxy radical, or by a fluorine atom, (ii) an n-propyl, n-butyl, n-pentyl, n-hexyl, n-heptyl, n-octyl, n-nonyl, sec-butyl, —$(CH_2)_2$—OH, —$(CH_2)_3$—OH or —$(CH_2)_4$—OH radical, (iii) a —$CH_2$-cyclopropyl, —$CH_2$-cyclohexyl, cyclopentyl, cyclohexyl or cycloheptyl radical, (iv) a radical —$(CH_2)_n$—Ar wherein n is equal to 1 or 2 and Ar is an unsubstituted phenyl radical or phenyl monosubstituted, preferably in the para position, by a methyl radical, or a fluorine atom.

Preferably, when $R_3$ is bonded to $R_6$ and —$R_3$-$R_6$— is —$C(O)CH_2$—, then $R_5$ is a phenyl radical or phenyl monosubstituted, preferably in the meta or para position, by a methyl, ethyl, n-butyl or benzyloxy radical, or by a fluorine atom.

According to the present invention, amongst the compounds of formula (I) such as defined above, particularly preferred compounds are those which have one or a combination of the following characteristics:

$R_1$ and $R_2$ are identical and are each an isopropyl radical, $R_3$ is bonded to $R_6$ and —$R_3$-$R_6$— is —$C(O)$—, R₄ and R'₄ are bonded to one another and together form, with the carbon atom from which they depend, a cyclohexyl group.

The compounds below, as well as their pharmaceutically acceptable salts, solvates and hydrates and their conformers or rotamers are particularly preferred:

N-(2,6-Diisopropylphenyl)-2-(2-oxo-1-phenyl-1,3-diazaspiro[4.5]dec-3-yl)-acetamide, compound (I.1) with R=H; R₁=R₂=iPr; —R₃-R₆═══C(O)—; R₄ and R'₄ are bonded to one another to form a cyclohexyl; R₅=Ph

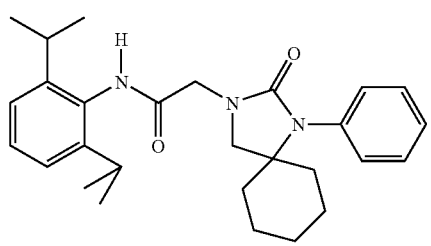
(I.1)

N-(2,6-Diisopropylphenyl)-2-(1-phenyl-1,3-diazaspiro[4.5]dec-3-yl)-acetamide, compound (I.2) with R=H; R₁=R₂=iPr; —R₃-R₆═══CH₂—; R₄ and R'₄ are bonded to one another to form a cyclohexyl; R₅=Ph

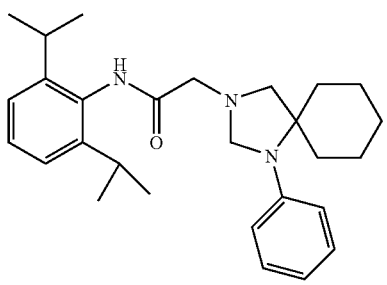
(I.2)

N-(2,6-Diisopropylphenyl)-2-(2,2-dioxo-1-phenyl-2lambda*6*-thia-1,3-di-azaspiro[4.5]dec-3-yl)acetamide, compound (I.3) with R=H; R₁=R₂=iPr; —R₃-R₆═══SO₂—; R₄ and R'₄ are bonded to one another to form a cyclohexyl; R₅=Ph

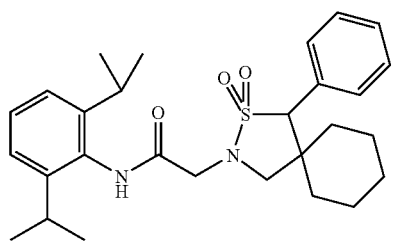
(I.3)

N-(2,6-Diisopropylphenyl)-2-[(1-phenylaminocyclohexylmethyl)amino]-acetamide, compound (I.4) with R=H; R₁=R₂=iPr; R₃=H; R₄ and R'₄ are bonded to one another to form a cyclohexyl; R₅=Ph, R₆=H

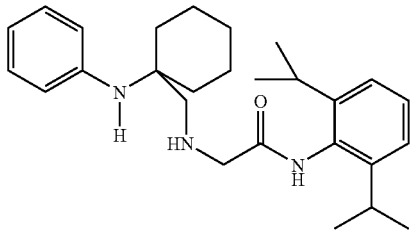
(I.4)

N-(2,6-Diisopropylphenyl)-2-(2,2-dioxo-1-p-tolyl-2lambda*6*-thia-1,3-di-azaspiro[4.5]dec-3-yl)acetamide, compound (I.5) with R=H; R₁=R₂=iPr; —R₃-R₆═══SO₂—; R₄ and R'₄ are bonded to one another to form a cyclohexyl; R₅=4-Me-Ph

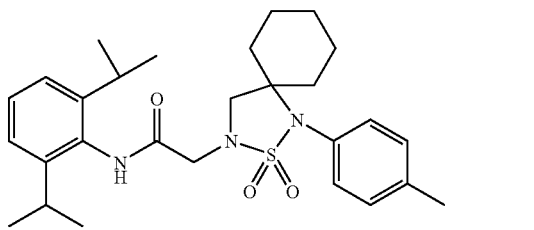
(I.5)

N-(2,6-Diisopropylphenyl)-2-(2-oxo-1-p-tolyl-1,3-diazaspiro[4.5]dec-3-yl)-acetamide, compound (I.6) with R=H; R₁=R₂=iPr; —R₃-R₆═══C(O)—; R₄ and R'₄ are bonded to one another to form a cyclohexyl; R₅=4-Me-Ph

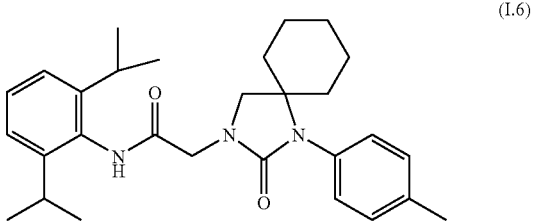 [SMILES: Cc1ccc(N2C(=O)N(CC(=O)Nc3c(C(C)C)cccc3C(C)C)CC23CCCCC3)cc1]
(I.6)

N-(2,6-Diisopropylphenyl)-2-(3-oxo-1-phenyl-1,4-diazaspiro[5.5]undec-4-yl)acetamide, compound (I.7) with R=H; R₁=R₂=iPr; —R₃-R₆═══C(O)—CH₂—; R₄ and R'₄ are bonded to one another to form a cyclohexyl; R₅=Ph

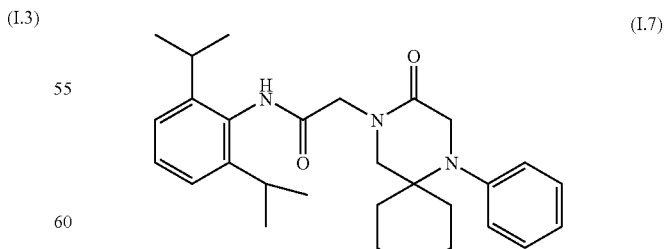
(I.7)

tert-Butyl [(2,6-diisopropylphenylcarbamoyl)methyl]-(1-phenylamino-cyclohexylmethyl)carbamate, compound (I.8) with R=H; R₁=R₂=iPr; R₃=C(O)R₇; R₄ and R'₄ are bonded to one another to form a cyclohexyl; R₅=Ph, R₆=H, R₇=OᵗBu

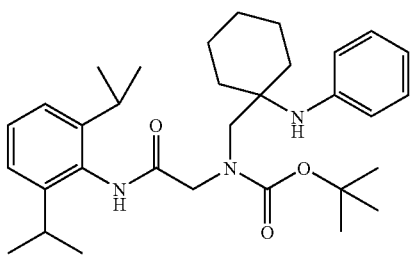

N-(2,6-Diisopropylphenyl)-2-[1-(4-ethylphenyl)-2-oxo-1,3-diazaspiro-[4.5]dec-3-yl]acetamide, compound (I.9) with R=H; $R_1=R_2$=iPr; =—C(O)—; $R_4$ and $R'_4$ are bonded to one another to form a cyclohexyl; $R_5$=4-Et-Ph (I.9)

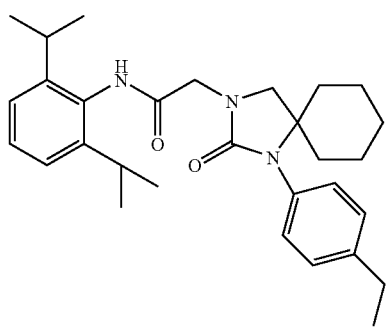

2-[1-(4-Butylphenyl)-2-oxo-1,3-diazaspiro[4.4]non-3-yl]-N-(2,6-diisopropyl-phenyl)acetamide, compound (I.10) with R=H; $R_1=R_2$=iPr; —$R_3$-$R_6$—=—C(O)—; $R_4$ and $R'_4$ are bonded to one another to form a cyclopentyl; $R_5$=4-Bu-Ph (I.10)

N-(2,6-Diisopropylphenyl)-2-[1-(4-ethylphenyl)-2-oxo-1,3-diazaspiro-[4.4]non-3-yl]acetamide, compound (I.11) with R=H; $R_1=R_2$=iPr; —$R_3$-$R_6$—=—C(O)—; $R_4$ and $R'_4$ are bonded to one another to form a cyclopentyl; $R_5$=4-Et-Ph (I.11)

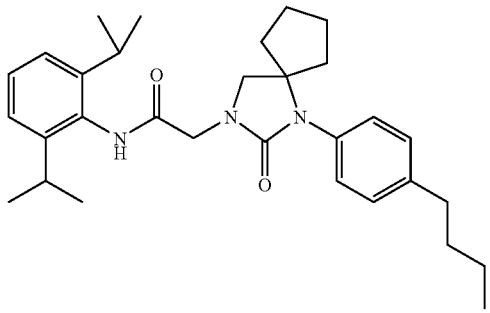

2-[1-(4-Butylphenyl)-2-oxo-1,3-diazaspiro[4.5]dec-3-yl]-N-(2,6-diisopropyl-phenyl)acetamide, compound (I.12) with R=H; $R_1=R_2$=iPr; —$R_3$-$R_6$—=—C(O)—; $R_4$ and $R'_4$ are bonded to one another to form a cyclohexyl; $R_5$=4-Bu-Ph (I.12)

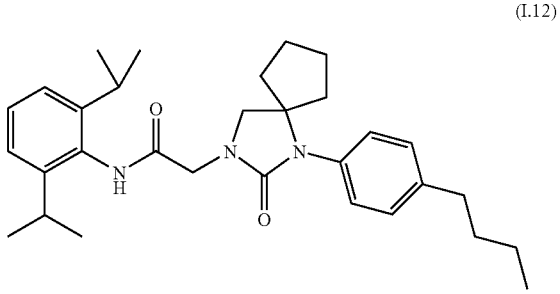 [SMILES: CCCCc1ccc(N2C(=O)N(CC(=O)Nc3c(C(C)C)cccc3C(C)C)CC23CCCC3)cc1]

2-(4,4-Diethyl-2-oxo-3-p-tolylimidazolidin-1-yl)-N-(2,6-diisopropylphenyl)-acetamide, compound (I.13) with R=H; $R_1=R_2$=iPr; —$R_3$-$R_6$—=—C(O)—; $R_4$=$R'_4$=Et; $R_5$=4-Me-Ph (I.13)

2-[1-(4-Benzyloxyphenyl)-2-oxo-1,3-diazaspiro[4.4]non-3-yl]-N-(2,6-diiso-propylphenyl)acetamide, compound (1.14) with R=H; $R_1=R_2$=iPr; —$R_3$-$R_6$—α—C(O)—; $R_4$ and $R'_4$ are bonded to one another to form a cyclopentyl; $R_5$=4-BnO-Ph (I.14)

2-[1-(4-Benzyloxyphenyl)-2-oxo-1,3-diazaspiro[4.5]dec-3-yl]-(2,6-diiso-propylphenyl)acetamide, compound (I.15) with R=H; $R_1=R_2$=iPr; —$R_3$-$R_6$—=—C(O)—; $R_4$ and $R'_4$ are bonded to one another to form a cyclohexyl; $R_5$=4-BnO-Ph

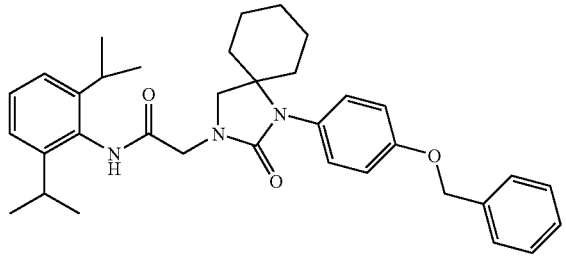

N-(2,6-Diethylphenyl)-2-(2-oxo-1-p-tolyl-1,3-diazaspiro[4.5]dec-3-yl)-acetamide, compound (I.16) with R=H; $R_1=R_2=Et$; —$R_3$-$R_6$══C(O)—; $R_4$ and $R'_4$ are bonded to one another to form a cyclohexyl; $R_5$=4-Me-Ph

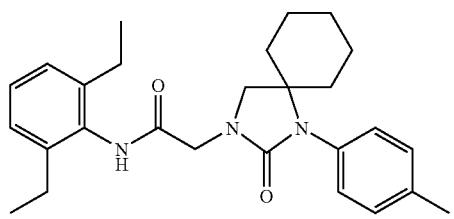

N-(2-tert-Butyl-6-methylphenyl)-2-(2-oxo-1-p-tolyl-1,3-diazaspiro[4.5]dec-3-yl)acetamide, compound (I.17) with R=H; $R_1$=Me; $R_2$=tBu; —$R_3$-$R_6$══C(O)—; $R_4$ and $R'_4$ are bonded to one another to form a cyclohexyl; $R_5$=4-Me-Ph

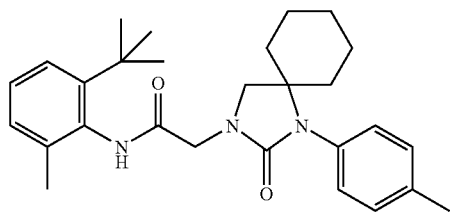

N-(2,6-Diisopropylphenyl)-2-(2-oxo-4,4-dipropyl-3-p-tolylimidazolidin-1-yl)-acetamide, compound (I.18) with R=H; $R_1=R_2=iPr$; —$R_3$-$R_6$══C(O)—; $R_4=R'_4$=nPr; $R_5$=4-Me-Ph

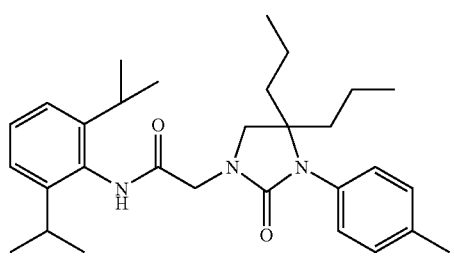

N-(2,6-Diisopropylphenyl)-2-(3-oxo-1-p-tolyl-1,4-diazaspiro[5.5]undec-4-yl)acetamide, compound (I.19) with R=H; $R_1=R_2=iPr$; —$R_3$-$R_6$══C(O)—; $R_4$ and $R'_4$ are bonded to one another to form a cyclohexyl; $R_5$=4-Me-Ph

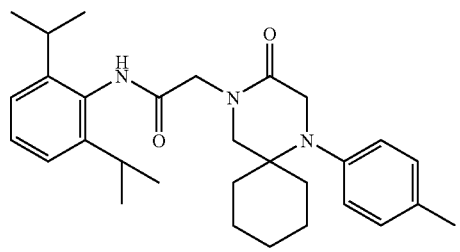

N-(2,6-Diisopropylphenyl)-2-[1-(4-fluorophenyl)-2-oxo-1,3-diazaspiro[4.5]dec-3-yl]acetamide, compound (I.20) with R=H; $R_1=R_2=iPr$; —$R_3$-$R_6$══C(O)—; $R_4$ and $R'_4$ are bonded to one another to form a cyclohexyl; $R_5$=4-F-Ph

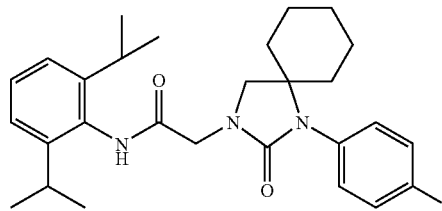

N-(2,6-Diisopropylphenyl)-2-(2-oxo-1-p-tolyl-1,3-diazaspiro[4.4]non-3-yl)-acetamide, compound (I.21) with R=H; $R_1=R_2=iPr$; —$R_3$-$R_6$══C(O)—; $R_4$ and $R'_4$ are bonded to one another to form a cyclopentyl; $R_5$=4-Me-Ph

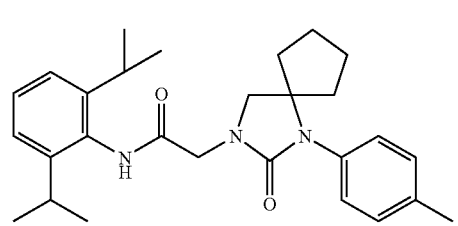

N-(2,6-Diisopropylphenyl)-2-[1-(4-fluorophenyl)-2-oxo-1,3-diazaspiro[4.4]non-3-yl]acetamide, compound (I.22) with R=H; $R_1=R_2=iPr$; —$R_3$-$R_6$══C(O)—; $R_4$ and $R'_4$ are bonded to one another to form a cyclopentyl; $R_5$=4-F-Ph

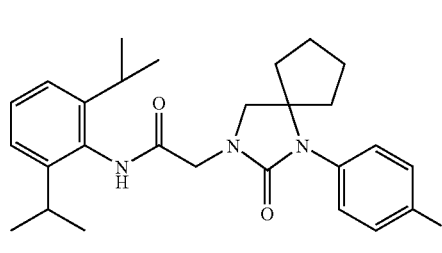

N-(2,6-Diisopropylphenyl)-2-(2-oxo-1-m-tolyl-1,3-diazaspiro[4.5]dec-3-yl)-acetamide, compound (I.23) with R=H; $R_1=R_2=iPr$; —$R_3$-$R_6$══C(O)—; $R_4$ and $R'_4$ are bonded to one another to form a cyclohexyl; $R_5$=3-Me-Ph (I.23)

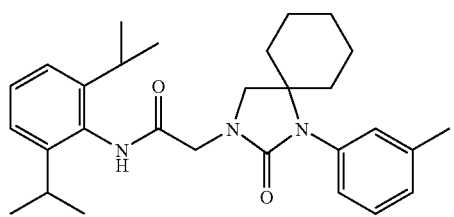

N-(2,6-Diisopropylphenyl)-2-(2-oxo-1-propyl-1,3-diazaspiro[4.5]dec-3-yl)-acetamide, compound (I.24) with R=H; $R_1=R_2=iPr$; —$R_3$-$R_6$=—C(O)—; $R_4$ and $R'_4$ are bonded to one another to form a cyclohexyl; $R_5$=n-Pr (I.24)

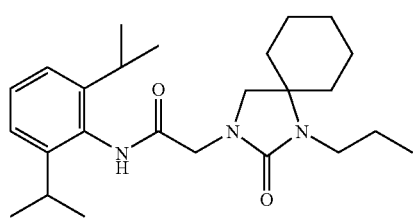

2-(1-Butyl-2-oxo-1,3-diazaspiro[4.5]dec-3-yl)-N-(2,6-diisopropylphenyl)-acetamide, compound (I.25) with R=H; $R_1=R_2=iPr$; —$R_3$-$R_6$=—C(O)—; $R_4$ and $R'_4$ are bonded to one another to form a cyclohexyl; $R_5$=n-Bu (I.25)

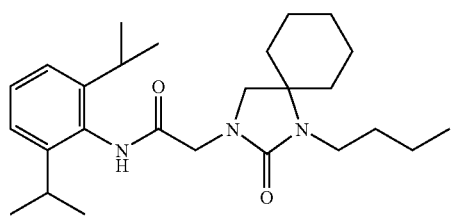

N-(2,6-Diisopropylphenyl)-2-(2-oxo-1-pentyl-1,3-diazaspiro[4.5]dec-3-yl)-acetamide, compound (I.26) with R=H; $R_1=R_2=iPr$; —$R_3$-$R_6$=—C(O)—; $R_4$ and $R'_4$ are bonded to one another to form a cyclohexyl; $R_5$=n-Pent (I.26)

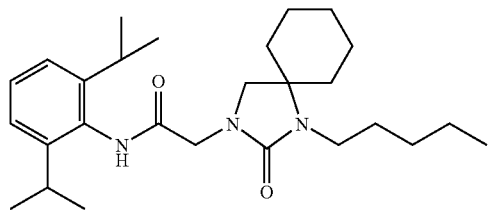

N-(2,6-Diisopropylphenyl)-2-(1-hexyl-2-oxo-1,3-diazaspiro[4.5]dec-3-yl)-acetamide, compound (I.27) with R=H; $R_1=R_2=iPr$; —$R_3$-$R_6$=—C(O)—; $R_4$ and $R'_4$ are bonded to one another to form a cyclohexyl; $R_5$=n-Hex (I.27)

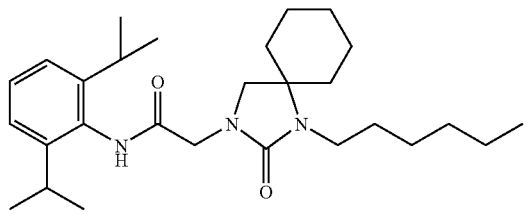

N-(2,6-Diisopropylphenyl)-2-(1-heptyl-2-oxo-1,3-diazaspiro[4.5]dec-3-yl)-acetamide, compound (I.28) with R=H; $R_1=R_2=iPr$; —$R_3$-$R_6$=—C(O)—; $R_4$ and $R'_4$ are bonded to one another to form a cyclohexyl; $R_5$=n-Hept (I.28)

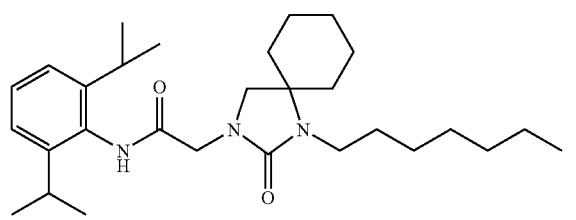

N-(2,6-Diisopropylphenyl)-2-(1-octyl-2-oxo-1,3-diazaspiro[4.5]dec-3-yl)-acetamide, compound (I.29) with R=H; $R_1=R_2=iPr$; —$R_3$-$R_6$=—C(O)—; $R_4$ and $R'_4$ are bonded to one another to form a cyclohexyl; $R_5$=n-Oct (I.29)

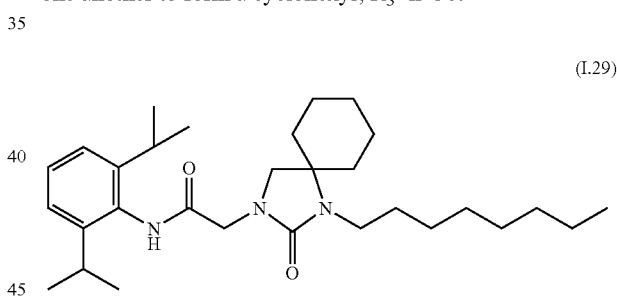

N-(2,6-Diisopropylphenyl)-2-(1-nonyl-2-oxo-1,3-diazaspiro[4.5]dec-3-yl)-acetamide, compound (I.30) with R=H; $R_1=R_2=iPr$; —$R_3$-$R_6$=—C(O)—; $R_4$ and $R'_4$ are bonded to one another to form a cyclohexyl; $R_5$=n-Non (I.30)

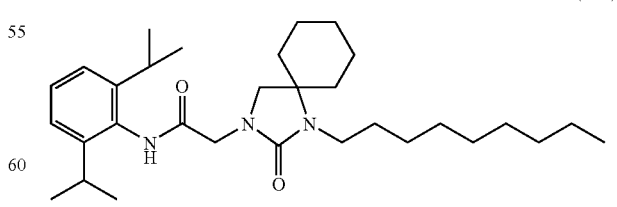

N-(2,6-Diisopropylphenyl)-2-(1-isobutyl-2-oxo-1,3-diazaspiro[4.5]dec-3-yl)-acetamide, compound (I.31) with R=H; $R_1=R_2=iPr$; —$R_3$-$R_6$=—C(O)—; $R_4$ and $R'_4$ are bonded to one another to form a cyclohexyl; $R_5$=2-Me-Pr

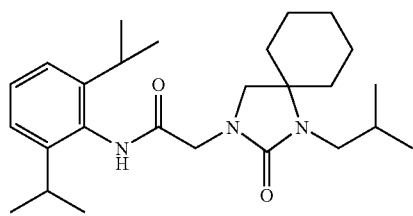

(I.31)

2-(1-Cyclopropylmethyl-2-oxo-1,3-diazaspiro[4.5]dec-3-yl)-N-(2,6-diiso-propylphenyl)acetamide, compound (I.32) with R=H; R₁=R₂=iPr; —R₃-R₆══C(O)—; R₄ and R'₄ are bonded to one another to form a cyclohexyl; R₅=CH₂-cyclopropyl

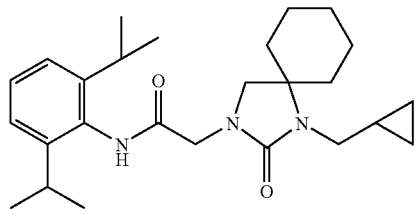

(I.32)

2-(1-Cyclohexylmethyl-2-oxo-1,3-diazaspiro[4.5]dec-3-yl)-N-(2,6-diiso-propylphenyl)acetamide, compound (I.33) with R=H; R₁=R₂=iPr; —R₃-R₆══C(O)—; R₄ and R'₄ are bonded to one another to form a cyclohexyl; R₅=CH₂-cyclohexyl

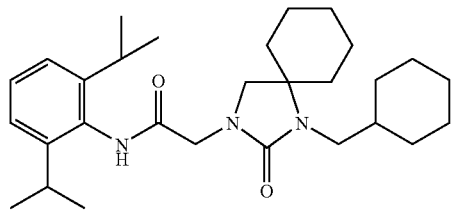

(I.33)

2-(1-Cyclopentyl-2-oxo-1,3-diazaspiro[4.5]dec-3-yl)-N-(2,6-diisopropyl-phenyl)acetamide, compound (I.34) with R=H; R₁=R₂=iPr; —R₃-R₆══C(O)—; R₄ and R'₄ are bonded to one another to form a cyclohexyl; R₅=cyclopentyl

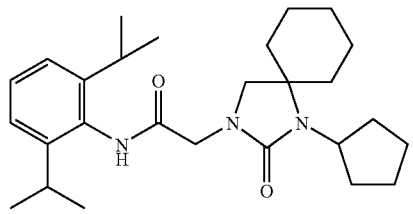

(I.34)

2-(1-Cyclohexyl-2-oxo-1,3-diazaspiro[4.5]dec-3-yl)-N-(2,6-diisopropyl-phenyl)acetamide, compound (I.35) with R=H; R₁=R₂=iPr; —R₃-R₆══C(O)—; R₄ and R'₄ are bonded to one another to form a cyclohexyl; R₅=cyclohexyl

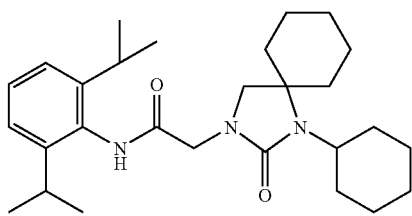

(I.35)

2-(1-Cycloheptyl-2-oxo-1,3-diazaspiro[4.5]dec-3-yl)-N-(2,6-diisopropyl-phenyl)acetamide, compound (I.36) with R=H; R₁=R₂=iPr; —R₃-R₆══C(O)—; R₄ and R'₄ are bonded to one another to form a cyclohexyl; R₅=cycloheptyl

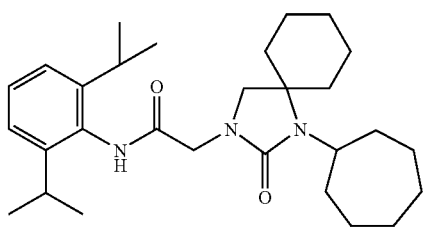

(I.36)

2-[Acetyl-(1-phenylaminocyclohexylmethyl)amino]-N-(2,6-diisopropyl-phenyl)acetamide, compound (I.37) with R=H; R₁=R₂=iPr; R₃=C(O)R₇; R₄ and R'₄ are bonded to one another to form a cyclohexyl; R₅=Ph, R₆=H, R₇=Me

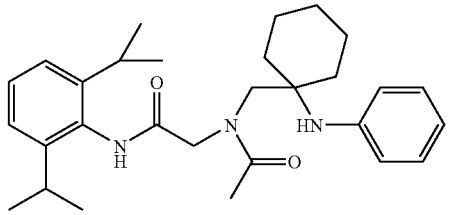

(I.37)

N-(2,6-Diisopropylphenyl)-2-(2-oxo-1-phenethyl-1,3-diazaspiro[4.5]dec-3-yl)acetamide, compound (I.38) with R=H; R₁=R₂=iPr; —R₃-R₆══C(O)—; R₄ and R'₄ are bonded to one another to form a cyclohexyl; R₅=(CH₂)ₙ—Ar, n=2, Ar=Ph

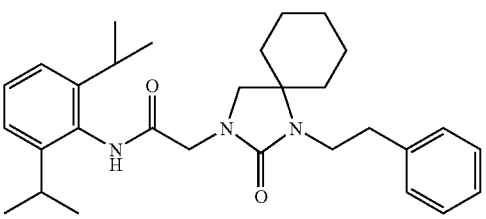

(I.38)

2-(1-Benzyl-2-oxo-1,3-diazaspiro[4,5]dec-3-yl)-N-(2,6-diisopropylphenyl)-acetamide, compound (I.39) with R=H; R₁=R₂=iPr; —R₃-R₆══C(O)—; R₄ and R'₄ are bonded to one another to form a cyclohexyl; R₅=(CH₂)n-Ar, n=1, Ar=Ph

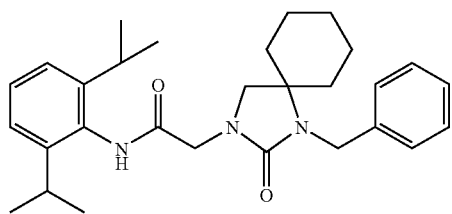

(I.39)

N-(2,6-Diisopropylphenyl)-2-[1-(4-methylbenzyl)-2-oxo-1,3-diazaspiro[4.5]dec-3-yl]acetamide, compound (I.40) with R=H; $R_1=R_2=$iPr; $-R_3-R_6-=-C(O)-$; $R_4$ and $R'_4$ are bonded to one another to form a cyclohexyl; $R_5=(CH_2)$n-Ar, n=1, Ar=4-Me-Ph

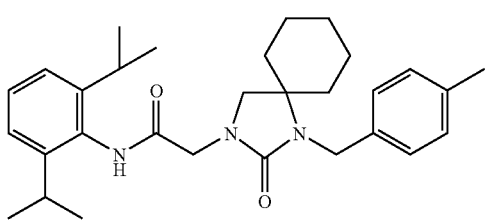

(I.40)

N-(2,6-Diisopropylphenyl)-2-[1-(4-fluorobenzyl)-2-oxo-1,3-diazaspiro[4.5]dec-3-yl]acetamide, compound (I.41) with R=H; $R_1=R_2=$iPr; $-R_3-R_6-=-C(O)-$; $R_4$ and $R'_4$ are bonded to one another to form a cyclohexyl; $R_5=(CH_2)$n-Ar, n=1, Ar=4-F-Ph

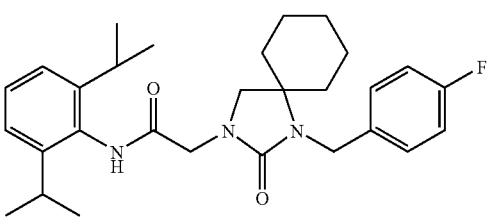

(I.41)

N-(2,6-Diisopropylphenyl)-2-(2-oxo-1-(3-hydroxy)propyl-1,3-diazaspiro[4.5]dec-3-yl)acetamide (I.42) with R=H; $R_1=R_2=$iPr; $-R_3-R_6-=-C(O)-$; $R_4$ and $R'_4$ are bonded to one another to form a cyclohexyl; $R_5=(CH_2)_3-OH$

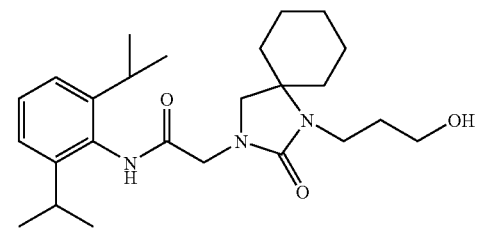

(I.42)

N-(2,6-Diisopropylphenyl)-2-(2-oxo-1-(4-hydroxy)butyl-1,3-diazaspiro[4.5]dec-3-yl)acetamide (I.43) with R=H; $R_1=R_2=$iPr; $-R_3-R_6-=-C(O)-$; $R_4$ and $R'_4$ are bonded to one another to form a cyclohexyl; $R_5=(CH_2)_4-OH$

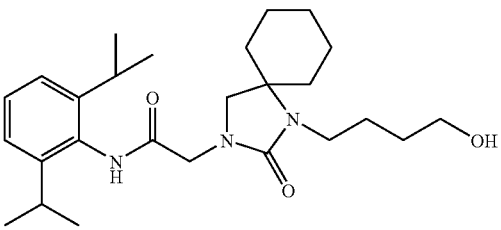

(I.43)

N-(2,6-Diisopropylphenyl)-2-(2-oxo-1-(2-hydroxy)ethyl-1,3-diazaspiro[4.5]dec-3-yl)acetamide (I.44) with R=H; $R_1=R_2=$iPr; $-R_3-R_6-=-C(O)-$; $R_4$ and $R'_4$ are bonded to one another to form a cyclohexyl; $R_5=(CH_2)_2-OH$

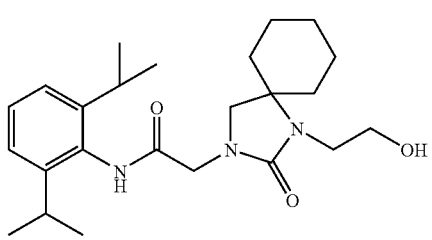

(I.44)

The salts of the compounds of formula (I) according to the invention are prepared according to techniques well known to one skilled in the art. They comprise the salts with inorganic acids or organic acids which allow a suitable separation or a crystallization of the compounds of formula (I), as well as pharmaceutically acceptable salts. As far as an appropriate acid is concerned, it is possible to mention: picric acid, oxalic acid or an optically active acid, for example a tartaric acid, a dibenzoyltartaric acid, a mandelic acid or a camphorsulfonic acid, and those which form physiologically acceptable salts, such as the hydrochloride, the hydrobromide, the sulfate, the hydrogensulfate, the dihydrogenphosphate, the maleate, the fumarate, and the 2-naphthalenesulfonate, the paratoluenesulfonate, the hydrochloride being preferred.

The solvates or hydrates may be obtained directly from the synthesis process, the compound (I) being isolated in the form of a hydrate, for example a mono- or hemihydrate or a solvate of the reaction or purification solvent.

The compounds of formula (I) can be purified according to any conventional purification technique, for example by crystallization or purification by column chromatography.

When a compound of formula (I) according to the invention has one or more asymmetric carbons, the optical isomers of this compound are integral parts of the invention. The compounds of formula (I) can thus be in the form of a pure isomer or of a mixture of isomers in any proportion.

Conformers are understood as meaning an element of a set of conformational stereoisomers of which each is characterized by a conformation corresponding to a distinct minimum potential energy of the molecular entity.

Rotamer means an element of a set of conformers resulting from a restricted rotation around a single bond.

The compounds of formula (I) according to the invention can be prepared according to SCHEME 1 below, in which R, $R_1, R_2, R_3, R_4, R'_4$ and $R_5$ are as defined for the compounds of formula (I):

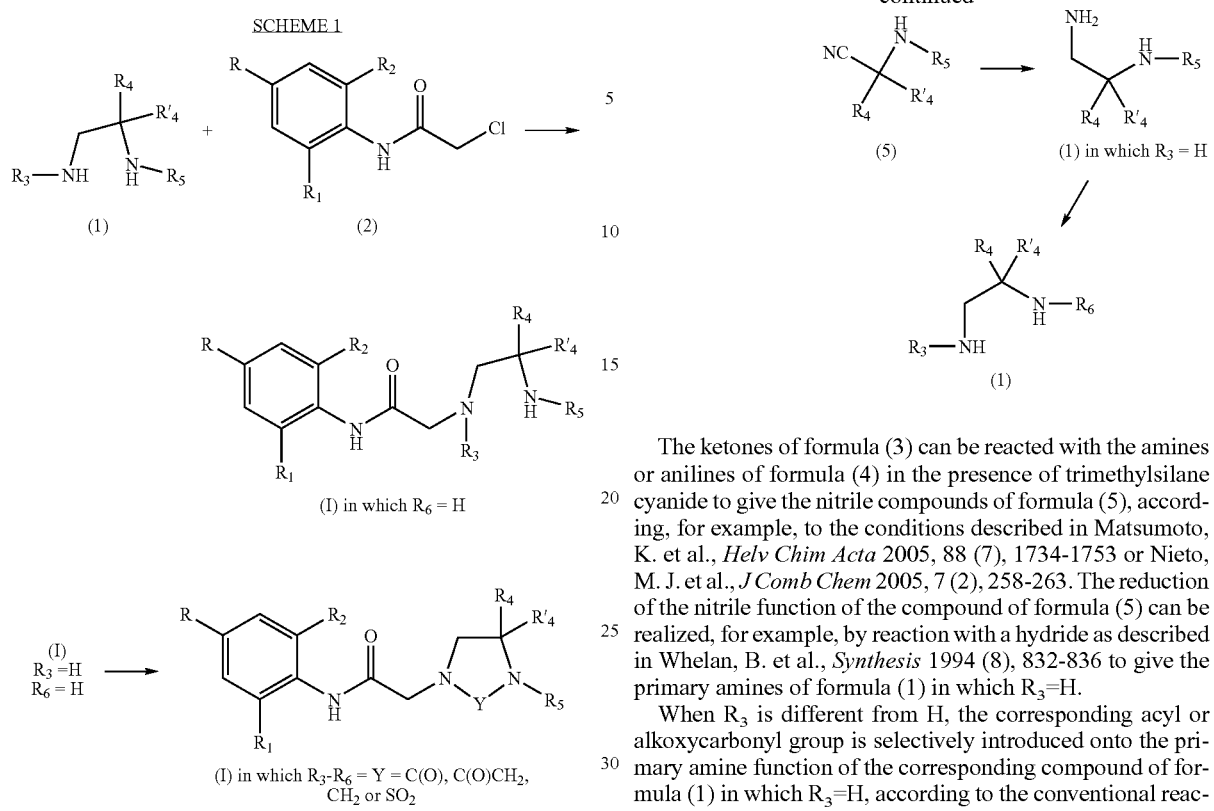

The compounds of the general formula (I) in which $R_6$=H can be prepared by substitution of the precursors of formula (1) on the chloroacetamides of formula (2), by analogy, for example, with the reactions described by Lee, A.-R. et al., in *J Heterocycl Chem* 1995, 32 (1), 1, by Maligres, P. E. et al., in *J Heterocycl Chem* 2003, 40 (2), 229, by Tverdokhlebov, A. V. et al., in *Synthesis* 2003, (17), 2632 or by Das, S. K. et al., in *Bioorg Med Chem Lett*, 2002, 12 (24), 3579.

When $R_3$ and $R_6$ are bonded to one another and correspond to Y=C(O), C(O)CH$_2$, CH$_2$ or SO$_2$, the compounds of formula (I) can be obtained starting from compounds of corresponding formula (I) in which $R_3$=$R_6$=H subjected to a cyclization reaction, for example, in the presence of triphosgene as described in Koenigsberger, K. et al., *Tetrahedron: Asymmetry* 1997, 8 (14), 2347, in the presence of chloroacetyl chloride as described in Chen, Z. et al., *Synth Commun* 2006, 36 (4), 473, in the presence of formaldehyde as described in Del Giudice, M. R. et al., *J Heterocycl Chem* 1990, 27, 967 or in the presence of sulfamide as described in Sparey, T., et al., *Bioorg Med Chem Lett* 2005, 15 (19) 4212.

The compounds of general formula (1) can be prepared according to SCHEME 2 below, in which $R_3$, $R_4$, $R'_4$ and $R_5$ are such as defined for the compounds of formula (I):

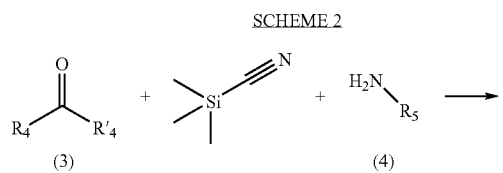

The ketones of formula (3) can be reacted with the amines or anilines of formula (4) in the presence of trimethylsilane cyanide to give the nitrile compounds of formula (5), according, for example, to the conditions described in Matsumoto, K. et al., *Helv Chim Acta* 2005, 88 (7), 1734-1753 or Nieto, M. J. et al., *J Comb Chem* 2005, 7 (2), 258-263. The reduction of the nitrile function of the compound of formula (5) can be realized, for example, by reaction with a hydride as described in Whelan, B. et al., *Synthesis* 1994 (8), 832-836 to give the primary amines of formula (1) in which $R_3$=H.

When $R_3$ is different from H, the corresponding acyl or alkoxycarbonyl group is selectively introduced onto the primary amine function of the corresponding compound of formula (1) in which $R_3$=H, according to the conventional reactions of amide or carbamate formation, for example by conforming to the conditions described in Sun, L.-Q. et al., *Bioorg Med Chem Lett* 2004, 14 (20), 5157 (acyl) or in Cachoux, F. et al., *Synth Commun* 2001, 31 (24), 3759 and Bourrain, S. et al., *Bioorg Med Chem Lett* 1999, 9 (23), 3369 (alkoxycarbonyl).

The chloroacetamides of formula (2) can be prepared according to an amidification reaction starting from anilines of formula (6), in the presence of a base and chloroacetyl chloride, for example as described in Davion, Y. et al., *Heterocycles* 2004, 63 (5), 1093 or Juaristi, E. et al. *J Org Chem* 1999, 64 (8), 2914 allows them to be obtained as described in SCHEME 3 below, in which $R_1$, $R_2$ and $R_3$ are such as defined for the compounds of formula (I):

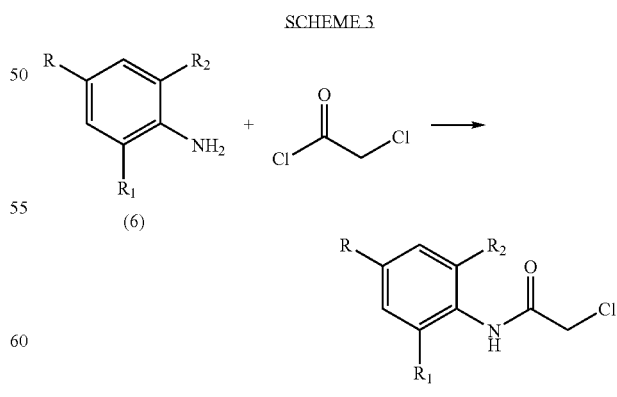

The anilines (6) are commercial compounds or are prepared according to techniques well known to one skilled in the art.

The functional groups optionally present in the reaction intermediates used in the process can be protected, either in a permanent manner or in a temporary manner, by protective groups which ensure an univocal synthesis of the expected compounds. The protection and deprotection reactions are carried out according to techniques well known one skilled in the art. A temporary protective group of amines, of alcohols or of carboxylic acids means the protective groups such as those described in "Protective Groups in Organic Chemistry", ed McOmie J. W. F., Plenum Press, 1973, "Protective Groups in Organic Synthesis", 2nd edition, Greene T. W. and Wuts P. G. M., ed John Wiley and Sons, 1991 and in "Protecting Groups", Kocienski P. J., Georg Thieme Verlag.

The compounds (I) according to the invention, as well as their pharmaceutically acceptable salts, solvates and/or hydrates, have inhibitory properties on the enzyme SOAT-1. This inhibitory activity on the enzyme SOAT-1 is measured according to a primary enzymatic test HepG2, as described in Example 16. The preferred compounds according to the present invention have a concentration allowing 50% of the response of the enzyme ($IC_{50}$) to be inhibited at less than or equal to 1000 nM, preferably at less than or equal to 300 nM, advantageously at less than or equal to 100 nM, or even at 50 nM.

The present invention also features medicaments, comprising the compounds of formula (I) such as described above, as well as their pharmaceutically acceptable salts, pharmaceutically acceptable solvates and/or hydrates.

The present invention also features the formulation of at least one compound of formula (I), and also its salts, pharmaceutically acceptable solvates and/or hydrates, into medicaments useful to prevent and/or to treat the disorders of the sebaceous gland such as hyperseborrhoea, acne, seborrheic dermatitis, atopic dermatitis or rosacea, ocular pathologies such as ocular rosacea, disorders of the meibomian gland, such as blepharitis, meibonitis, chalazion, dry eye, conjunctivitis or keratoconjunctivitis, or even pathologies such as hypercholesterolaemia, arteriosclerosis or Alzheimer's disease. The compounds according to the invention are particularly suited for formulation into pharmaceutical compositions useful for the treatment of acne. The compounds according to the invention are thus suitable for utilization in the treatment of the pathologies listed above.

The present invention also features pharmaceutical or cosmetic compositions comprising, formulated into a physiologically acceptable carrier, at least one compound of formula (I) as defined above, or one of its salts, pharmaceutically acceptable solvates and/or hydrates. The compositions according to the invention thus comprise a physiologically acceptable carrier or at least one physiologically or pharmaceutically acceptable excipient, selected according to the cosmetic or pharmaceutical form desired and the selected mode of administration, whether regime or regimen.

Physiologically acceptable medium or carrier means a carrier compatible with the skin, the mucosa and/or the skin appendages.

The administration of the composition according to the invention can be effected by the enteral, parenteral, rectal, topical or ocular route, whether regime or regimen. Preferably, the pharmaceutical composition is in a form suitable for application by the topical route.

By the enteral route, the composition, more particularly the pharmaceutical composition, can be in the form of tablets, of capsules, of coated tablets, of syrups, of suspensions, of powders, of granules, of emulsions, of microspheres or nanospheres or lipid or polymeric vesicles allowing controlled liberation. By the parenteral route, the composition can be in the form of solutions or suspensions for perfusion or for injection.

The compounds according to the invention contain a compound according to the invention in sufficient quantity to elicit the therapeutic, prophylactic or cosmetic effect desired. The compounds according to the invention are generally administered in a daily dose of approximately 0.001 mg/kg to 100 mg/kg of body weight, in 1 to 3 doses. The compounds are administered by the systemic route at a concentration generally ranging from 0.001 to 10% by weight, preferably from 0.01 to 2% by weight, with respect to the weight of the composition.

By the topical route, the pharmaceutical composition according to the invention is more particularly useful for the treatment of the skin and of the mucosa and can be in the form of ointments, of creams, of milks, of pomades, of impregnated swabs, of syndets, of solutions, of gels, of sprays, of foams, of suspensions, of lotions, of sticks, of shampoos, or of washing bases. It can likewise be present in the form of suspensions of microspheres or nanospheres or lipid or polymeric vesicles or polymeric patches and hydrogels allowing controlled liberation. This composition by the topical route can be in anhydrous form, in aqueous form or in the form of an emulsion.

The compounds are administered by the topical route in a concentration generally ranging from 0.001 to 10% by weight, preferably from 0.01 to 2% by weight, with respect to the total weight of the composition.

The compounds of formula (I) according to the invention, as well as their salts, pharmaceutically acceptable solvates and/or hydrates, likewise are useful in the cosmetic field, in particular in body and hair hygiene and more particularly to combat or to prevent greasy skins or greasy hair or a greasy scalp.

The present invention thus features the cosmetic utilization of a composition comprising, in a physiologically acceptable carrier, at least one of the compounds of formula (I), optionally in the form of a salt, pharmaceutically acceptable solvate and/or hydrate, for body or hair hygiene.

The cosmetic compositions according to the invention containing, in a cosmetically acceptable carrier, at least one compound of formula (I) or one of its salts, pharmaceutically acceptable solvates and/or hydrates, can be, especially, in the form of a cream, of a milk, of a lotion, of a gel, of an ointment, of a pomade, of suspensions of microspheres or nanospheres or lipid or polymeric vesicles, of impregnated swabs, of solutions, of sprays, of foams, of sticks, of soaps, of shampoos or of washing bases.

The concentration of compounds of formula (I) in the cosmetic composition ranges from 0.001 to 3% by weight, with respect to the total weight of the composition.

The pharmaceutical and cosmetic compositions such as previously described can moreover contain inert, or even pharmacodynamically active, additives as far as the pharmaceutical compositions are concerned, or combinations of these additives, and especially:
  wetting agents;
  taste-improving agents;
  preservative agents such as the esters of parahydroxybenzoic acid;
  stabilizing agents;
  humidity-regulating agents;
  pH-regulating agents;
  osmotic pressure-modifying agents;
  emulsifying agents;
  UV-A and UV-B filters;

antioxidants, such as α-tocopherol, butylhydroxyanisole or butylhydroxy-toluene, superoxide dismutase, ubiquinol or certain metal chelating agents;

emollients;

hydrating agents such as glycerol, PEG 400, thiamorpholinone, and its derivatives or urea;

carotenoids and, especially, β-carotene;

α-hydroxy acids and α-ketoacids or their derivatives, such as the acids lactic, maleic, citric, glycolic, mandelic, tartaric, glyceric, ascorbic, and their salts, amides or esters or β-hydroxy acids or their derivatives, such as salicylic acid as well as its salts, amides or esters.

Of course, one skilled in the art will take care to select optional compound(s) to add to these compositions in such a way that the properties advantageously attached intrinsically to the present invention are not, or not substantially, impaired by the envisaged addition.

Furthermore, generally, the same preferences as those indicated above for the compounds of formula (I) apply mutatis mutandis to the medicaments, cosmetic, and pharmaceutical compositions employing the compounds of the invention.

To further illustrate the present invention and the advantages thereof, the following specific examples are given, including those of biological activity, it being understood that same are intended only as illustrative and in nowise limitative. In said examples to follow, all parts and percentages are given by weight, unless otherwise indicated.

The following abbreviations are employed:
Ph=phenyl; Bn=benzyl; Me=methyl; Et=ethyl; Pr=propyl; iPr=isopropyl; tBu=tert-butyl; n-Pr=n-propyl; n-Bu=n-butyl; n-Pent=n-pentyl; n-Hex=n-hexyl; n-Hept=n-heptyl; n-Oct=n-octyl; n-Non=n-nonyl; M.p.=melting point.

PROCEDURES

Example 1

N-(2,6-Diisopropylphenyl)-2-(2-oxo-1-phenyl-1,3-diazaspiro[4.5]dec-3-yl)-acetamide, compound (I.1) with R=H; $R_1=R_2=iPr$; —$R_3$-$R_5$=—C(O)—; $R_4$ and $R'_4$ are bonded to one another to form a cyclohexyl; $R_5$=Ph

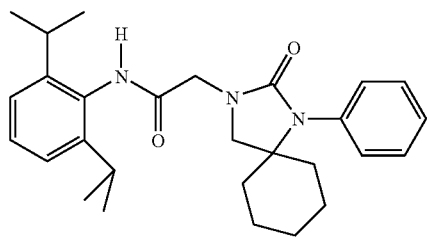

(a) Preparation of 1-Phenylaminocyclohexanecarbonitrile 1.4 ml (15.3 mmol) of aniline (starting product 1) are added to a solution of 1.3 ml (12.5 mmol) of cyclohexanone (starting product 2) in 20 ml of acetic acid at 0° C. The solution is stirred for a time and 1.9 ml (14.2 mmol) of trimethylsilyl cyanide are added. The reaction medium is stirred for one night at room temperature. It is then poured gently into an ice-cold ammonium hydroxide solution until the pH is basic and extracted with dichloromethane. The organic phases are collected and washed with water. They are dried over sodium sulfate. The residue is precipitated in dichloromethane and heptane. The solid is filtered and dried. 2.2 g of 1-phenylaminocyclohexanecarbonitrile are obtained in the form of a whitish solid. M.p.=67-9° C., yield=88%.

(b) Preparation of (1-Aminomethylcyclohexyl)phenylamine

A solution of 5 g (25 mmol) of 1-phenylaminocyclohexanecarbonitrile in 70 ml of ethyl ether is added drop by drop to 1.13 g (29.8 mmol) of lithium aluminum hydride in 30 ml of ethyl ether at 0° C. The mixture is stirred for 2 hours at 0° C. The reaction is stopped by the addition of 1.1 ml of water, 1.1 ml of 15% sodium hydroxide and then 3.5 ml of water. The medium is then filtered on Celite and the filtrate is evaporated. The residue is purified on silica gel (dichloromethane then dichloromethane/methanol 80/20, v/v). 2 g of (1-aminomethylcyclohexyl)phenylamine are obtained in the form of a brown oil. Yield=39%.

(c) Preparation of N-(2,6-Diisopropylphenyl)-2-[(1-phenylaminocyclohexylmethyl)amino]-acetamide 620 mg (2.45 mmol) of 2-chloro-N-(2,6-diisopropylphenyl)acetamide are added to 500 mg (2.45 mmol) of (1-aminomethylcyclohexyl)phenylamine in 10 ml of dimethylformamide. The reaction medium is stirred at 100° C. under microwave irradiation for 30 min. It is then poured into water and extracted with ethyl acetate. The organic phases are collected and washed with water. They are dried over sodium sulfate. The solvents are evaporated. The residue is chromatographed on silica gel (heptane/ethyl acetate 80/20, v/v). 580 mg of N-(2,6-diisopropylphenyl)-2-[(1-phenylaminocyclohexyl-methyl)amino]acetamide are obtained in the form of a beige solid. Yield=56%.

(d) Preparation of N-(2,6-Diisopropylphenyl)-2-(2-oxo-1-phenyl-1,3-diazaspiro[4.5]dec-3-yl)-acetamide 136 mg (0.46 mmol) of triphosgene are added to 10 ml of dichloro-methane. The medium is cooled to 0° C. and a solution of 580 mg (1.37 mmol) of N-(2,6-diisopropylphenyl)-2-[(1-phenylaminocyclohexyl-methyl)amino]acetamide and 260 µl (1.49 mmol) of diisopropylethylamine in 10 ml of dichloromethane are added drop by drop. The mixture is allowed to rise to room temperature and is stirred for one night. The medium is then poured into water and extracted with dichloromethane. The organic phases are collected and washed with water. They are dried over sodium sulfate. The solvents are evaporated. The residue is chromatographed on silica gel (heptane/ethyl acetate 80/20) and 485 mg of N-(2,6-diisopropylphenyl)-2-(2-oxo-1-phenyl-1,3-diazaspiro[4.5]dec-3-yl)acetamide are obtained in the form of a white solid after having been precipitated in dichloromethane and heptane, filtered and dried. M.p. 107-9° C., yield=79%.

$^1$H NMR (CDCl$_3$; 400 Mz): 0.95-1.05 (m, 1H); 1.23 (s, 6H); 1.24 (s, 6H); 1.52-1.60 (m, 5H); 1.75-1.85 (m, 2H); 1.86-1.95 (m, 2H); 3.09-3.13 (m, 2H); 3.59 (s, 2H); 4.13 (s, 2H); 7.18-7.20 (m, 4H); 7.28-7.43 (m, 4H); 8.05 (s, 1H).

Example 2

N-(2,6-Diisopropylphenyl)-2-(1-phenyl-1,3-diazaspiro[4.5]dec-3-yl)-acetamide, compound (I.2) with R=H;

$R_1=R_2=iPr$; —$R_3$-$R_6$=—$CH_2$—; $R_4$ and $R'_4$ are bonded to one another to form a cyclohexyl; $R_5$=Ph

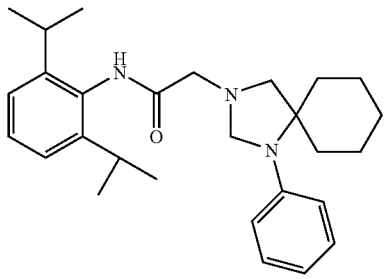

(I.2)

(a) Preparation of 1-Phenylaminocyclohexanecarboxylamide 5 g (25 mmol) of 1-phenylaminocyclohexanecarbonitrile (obtained according to Example 1a) are dissolved in 30 ml of concentrated sulfuric acid. The reaction medium is stirred at room temperature for 48 h. It is then gently poured into ice and the pH is set at 7-8 with sodium hydroxide and the mixture is extracted with ethyl acetate. The organic phases are collected and washed with water. They are dried over sodium sulfate. The solvents are evaporated and the residue is precipitated in dichloromethane and heptane and then filtered and dried.

5.2 g of 1-phenylaminocyclohexanecarboxylamide are obtained in the form of a white solid. M.p. 146-8° C., yield=95%.

(b) Preparation of (1-Aminomethylcyclohexyl)phenylamine 6.4 ml (12.8 mmol) of borane-dimethyl sulfate are added to a solution of 1.4 g (6.41 mmol) of 1-phenylaminocyclohexanecarboxylamide in 100 ml of THF. The reaction medium is stirred for 12 h at room temperature and then heated to reflux for 5 h. At room temperature, it is poured into water and extracted with ethyl acetate. The organic phases are collected and washed with water. They are dried over sodium sulfate. The solvents are evaporated. The residue is chromatographed on silica gel (dichloromethane/methanol 97/3 then 80/20, v/v). 830 mg of (1-aminomethylcyclohexyl)phenylamine are obtained in the form of a yellow oil. Yield=63%.

(c) Preparation of Ethyl [(1-phenylaminocyclohexylmethyl)amino]acetate 110 mg (2.69 mmol) of sodium hydride are added to a solution of 500 mg (2.45 mmol) of (1-aminomethylcyclohexyl)phenylamine in 20 ml of dimethyl formamide. The solution is stirred for 1 h at room temperature and 270 µl (2.45 mmol) of ethyl bromoacetate are added. The reaction medium is stirred at room temperature for 2 h. It is then poured into water and extracted with ethyl acetate. The organic phases are collected and washed with water. They are dried over sodium sulfate. The solvents are evaporated. The residue is chromatographed on silica gel (heptane then heptane/ethyl acetate 90/10, v/v). 530 mg of ethyl [(1-phenylamino-cyclohexylmethyl)amino]acetate are obtained in the form of a colorless oil. Yield=75%.

(d) Preparation of Ethyl (1-phenyl-1,3-diazaspiro[4.5]dec-3-yl)acetate 510 mg (1.75 mmol) of ethyl [(1-phenylaminocyclohexylmethyl)amino]-acetate are dissolved in 10 ml of dichloromethane and 10 ml of formaldehyde are added. The solution is heated to 100° C. with microwaves for 30 min. The medium is poured into dichloromethane and washed with water. The organic phases are collected and then dried over sodium sulfate. The solvents are evaporated. 520 mg of ethyl (1-phenyl-1,3-diazaspiro[4.5]dec-3-yl)acetate are obtained in the form of a colorless oil. Yield=98%.

(e) Preparation of (1-Phenyl-1,3-diazaspiro[4.5]dec-3-yl)acetic acid 200 mg (5 mmol) of sodium hydroxide are added to a solution of 510 mg (1.68 mmol) of ethyl (1-phenyl-1,3-diazaspiro[4.5]decyl)acetate in 10 ml of tetrahydrofuran. The solution is stirred for 4 h at room temperature. The medium is then poured into water, acidified to pH 1 with concentrated hydrochloric acid and extracted with ethyl acetate. The organic phases are collected and washed with water. They are dried over sodium sulfate. The solvents are evaporated. The product is triturated in heptane. 190 mg of (1-phenyl-1,3-diazaspiro[4.5]dec-3-yl)acetic acid are obtained in the form of a yellowish solid. M.p. 162-4° C., yield=41%.

(f) Preparation of N-(2,6-Diisopropylphenyl)-2-(1-phenyl-1,3-diazaspiro[4.5]dec-3-yl)-acetamide 130 µl (0.69 mmol) of 2,6-diisopropylaniline are added to a solution of 180 mg (0.65 mmol) of (1-phenyl-1,3-diazaspiro[4.5]dec-3-yl)acetic acid in 20 ml of dichloromethane. The solution is cooled to −10° C. and 132 mg (0.69 mmol) of 1-(3-dimethylaminopropyl)-3-ethylcarbodiimide are added. The medium is allowed to return to room temperature and stirred for 4 h and then at reflux for one day and again at room temperature for 5 days. The medium is then poured into water and extracted with dichloromethane. The organic phases are collected and washed with water. They are dried over sodium sulfate. The solvents are evaporated. The residue is chromatographed on silica gel (heptane/ethyl acetate 90/10, v/v). 25 mg of N-(2,6-diisopropylphenyl)-2-(1-phenyl-1,3-diazaspiro[4.5]dec-3-yl)acetamide are obtained in the form of a white solid. M.p. 151-3° C., yield=8.8%.

$^1$H NMR (CDCl$_3$; 400 Mz): 1.14 (s, 6H); 1.16 (s, 6H); 1.18-1.26 (m, 4H); 1.56-1.59 (m, 2H); 1.74-1.78 (m, 2H); 2.15-2.22 (m, 2H); 2.94-2.99 (m, 2H); 3.06 (s, 2H); 3.43 (s, 2H); 4.19 (s, 2H); 6.69-6.73 (m, 3H); 7.11-7.25 (m, 5H); 8.49 (s, 1H).

Example 3

N-(2,6-Diisopropylphenyl)-2-(2,2-dioxo-1-phenyl-2lambda*6*-thia-1,3-diaza-spiro[4.5]dec-3-yl]acetamide, compound (I.3) with R=H; $R_1$=$R_2$=iPr; $R_3$-$R_6$=—$SO_2$—; $R_4$ and $R'_4$ are bonded to one another to form a cyclohexyl; $R_5$=Ph

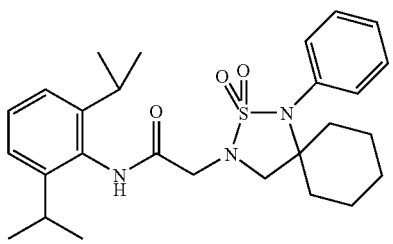

(I.3)

(a) Preparation of N-(1-Aminomethylcyclohexyl)-N-phenylmethanesulfonamide 105 mg (1.09 mmol) of sulfamide are added to a solution of 200 mg of (1-aminomethylcyclohexyl)phenylamine (obtained in Example 2b) in 5 ml of pyridine. The medium is stirred at room temperature for 24 h and then at reflux for 2 h. At room temperature, the medium is evaporated and taken up with ethyl acetate and washed with water. The organic phases are collected and dried over sodium sulfate. The solvents are evaporated. The residue is chromatographed on silica gel (ethyl acetate/heptane). 130 mg of N-(1-aminomethylcyclohexyl)-N-phenylmethanesulfonamide are obtained in the form of a yellow solid. Yield=50%.

(b) Preparation of 2-Chloro-N-(2,6-diisopropylphenyl)acetamide 222 ml (1.59 mol) of triethylamine are added to a solution of 300 ml (1.59 mol) of 2,6-diisopropylamine in 1 l of dichloromethane. The reaction mixture is cooled to 0° C. and then 127 ml (1.59 mmol) of chloroacetyl chloride are added drop by drop. Once the addition is finished, the ice bath is removed and the medium is stirred for 20 min. It is then poured into water and extracted with dichloromethane. The organic phases are collected and washed with water and then dried over sodium sulfate. The solvents are evaporated. The residue is filtered on a silica cake (eluent: dichloro-methane). The filtrate is evaporated and then triturated in heptane. 345 g of 2-chloro-N-(2,6-diisopropylphenyl)acetamide are obtained in the form of a white solid. Yield=85%. M.p. 146-8° C.

(c) Preparation of N-(2,6-Diisopropylphenyl)-2-(2,2-dioxo-1-phenyl-2lambda*6*-thia-1,3-diazaspiro[4.5]dec-3-yl]acetamide 75 mg (0.54 mmol) of potassium carbonate are added to a solution of 130 mg (0.49 mmol) of 1-phenyl-2-thia-1,3-diazaspiro[4.5]decane-2,2-dioxide and 136 mg (0.54 mmol) of 2-chloro-N-(2,6-diisopropylphenyl)-acetamide in 30 ml of dimethylformamide. The reaction medium is stirred at room temperature for one night and then it is heated to reflux for 6 hours and at room temperature for 48 h. The medium is then poured into water and extracted with ethyl acetate. The organic phases are collected and washed with water. They are dried over sodium sulfate. The solvents are evaporated. The residue is chromatographed on silica gel (heptane/ethyl acetate 90/10). 125 mg of N-(2,6-diisopropylphenyl)-2-(2,2-dioxo-1-phenyl-2-thia-1,3-diazaspiro[4.5]dec-3-yl]acetamide are obtained in the form of a yellow oil. The product is triturated in dichloromethane and plenty of heptane. A solid is obtained. M.p. 140-2° C., yield=53%.

$^1$H NMR (CDCl$_3$; 400 Mz): 0.95-1.05 (m, 1H); 1.24 (s, 6H); 1.25 (s, 6H); 1.28-1.59 (m, 5H); 1.79-1.82 (m, 2H); 2.01-2.04 (m, 2H); 3.06-3.11 (m, 2H); 3.68 (s, 2H); 4.09 (s, 2H); 7.22-7.24 (d, 2H, J=7.7 Hz); 7.33-7.34 (m, 1H); 7.43-7.49 (m, 5H); 8.12 (s, 1H).

Example 4

N-(2,6-Diisopropylphenyl)-2-[(1-phenylaminocyclohexylmethyl)amino]-acetamide, compound (I.4) with R=H; $R_1$=$R_2$=iPr; $R_3$=H; $R_4$ and $R'_4$ are bonded to one another to form a cyclohexyl; $R_5$=Ph, $R_6$=H

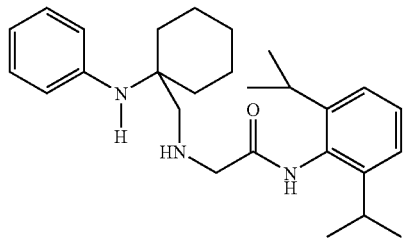

(I.4)

340 mg (1.34 mmol) of 2-chloro-N-(2,6-diisopropylphenyl)acetamide (obtained in Example 3/c) are added to 270 mg (1.32 mmol) of (1-amino-methylcyclohexyl)phenylamine (obtained in Example 2/b) in 10 ml of dimethylformamide. The reaction medium is stirred at 100° C. under microwave irradiation for 30 min. It is then poured into water and extracted with ethyl acetate. The organic phases are collected and washed with water and then dried over sodium sulfate. The solvents are evaporated. The residue is chromatographed on silica gel (heptane/ethyl acetate 80/20, v/v). 396 mg of N-(2,6-diisopropylphenyl)-2-[(1-phenylaminocyclohexylmethyl)-amino]acetamide are obtained in the form of a white solid. M.p. 104-6° C., yield=71%.

$^1$H NMR (CDCl$_3$; 400 Mz): 1.22 (s, 6H); 1.24 (s, 6H); 1.48-1.55 (m, 6H); 1.60 (m, 2H); 2.00-2.04 (m, 2H); 2.97 (s, 2H); 3.02-3.07 (m, 2H); 3.49 (s, 2H); 6.76-6.81 (m, 3H); 7.16-7.21 (m, 3H); 7.28-7.33 (m, 2H); 8.69 (s, 1H).

Example 5

N-(2,6-Diisopropylphenyl)-2-(2,2-dioxo-1-p-tolyl-2lambda*6*-thia-1,3-diaza-spiro[4.5]dec-3-yl)acetamide, compound (I.5) with R=H; $R_1$=$R_2$=iPr; $R_3$-$R_6$=—SO$_2$—; $R_4$ and $R'_4$ are bonded to one another to form a cyclohexyl; $R_5$=4-Me-Ph

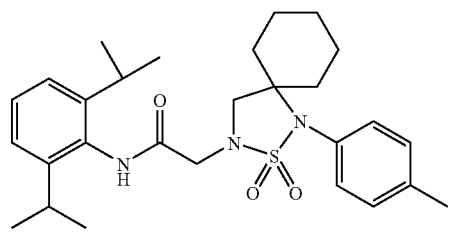

(I.5)

In a manner analogous to Example 3, by reaction of 0.128 g (0.457 mmol) of 1-p-tolyl-2-thia-1,3-diazaspiro[4.5]decane 2,2-dioxide with 0.137 g (0.502 mmol) of 2-chloro-N-(2,6-diisopropylphenyl)acetamide (obtained in Example 3/c) and 0.070 g (0.502 mmol) of potassium carbonate in 5 ml of dimethylformamide, 0.15 g of N-(2,6-diisopropylphenyl)-2-

(2,2-dioxo-1-p-tolyl-2-thia-1,3-diazaspiro[4.5]dec-3-yl)acetamide are obtained in the form of white solid. Yield=66%; m.p.=165° C.

¹H NMR (CDCl₃; 400 Mz): 1.24 (s, 6H); 1.25 (s, 6H); 1.26-1.40 (m, 3H); 1.46-1.50 (m, 2H); 1.59 (m, 1H); 1.78-1.82 (m, 2H); 1.99-2.03 (m, 2H); 2.42 (s, 3H); 3.08-3.11 (m, 2H); 3.66 (s, 2H); 4.08 (s, 2H); 7.21-7.23 (d, 2H, J=7.7 Hz); 7.26-7.36 (m, 5H); 8.11 (s, 1H).

The synthesis of Examples 6 and 9 to 15 is described by the tables below. The compounds are synthesized following the same reaction sequence as that described for Example 1, replacing the starting materials 1 and 2 of step (a) by the products indicated in the table below. The yields of these syntheses are homogeneous for the family of compounds considered.

| Ex. No. | IUPAC Name | Starting Product 1 | Starting Product 2 | M.p ° C. | NMR |
|---|---|---|---|---|---|
| 1 | N-(2,6-Diisopropylphenyl)-2-(2-oxo-1-phenyl-1,3-diazaspiro[4.5]dec-3-yl)acetamide | aniline | cyclohexanone | 107 | CDCl₃: 0.95-1.05 (m, 1H); 1.23 (s, 6H); 1.24 (s, 6H); 1.52-1.60 (m, 5H); 1.75-1.85 (m, 2H); 1.86-1.95 (m, 2H); 3.09-3.13 (m, 2H); 3.59 (s, 2H); 4.13 (s, 2H); 7.18-7.20 (m, 4H); 7.28-7.43 (m, 4H); 8.05 (s, 1H) |
| 6 | N-(2,6-Diisopropylphenyl)-2-(2-oxo-1-p-tolyl-1,3-diazaspiro[4.5]dec-3-yl)acetamide | p-Tolylamine | cyclohexanone | 146 | CDCl₃: 0.94-0.99 (m, 1H); 1.20 (s, 6H); 1.21 (s, 6H); 1.25-1.62 (m, 5H); 1.73-1.76 (m, 2H); 1.81-1.84 (m, 2H); 2.36 (s, 3H); 3.04-3.11 (m, 2H); 3.54 (s, 2H); 4.10 (s, 2H); 7.02-7.04 (d, 2H, J = 6.4 Hz); 7.16-7.25 (m, 4H); 7.26-7.30 (m, 1H); 8.06 (s |
| 9 | N-(2,6-Diisopropylphenyl)-2-[1-(4-ethylphenyl)-2-oxo-1,3-diazaspiro[4.5]dec-3-yl]-acetamide | 4-Ethyl-phenylamine | cyclohexanone | 95 | DMSO: 0.83-0.89 (m, 1H); 1.11 (s, 6H); 1.12 (s, 6H); 1.17-1.21 (t, 3H); 1.23-1.27 (m, 4H); 1.45-1.55 (m, 1H); 1.47-1.50 (m, 2H); 1.81-1.83 (m, 2H); 2.58-2,64 (m, 2H); 3.01-3.07 (m, 2H); 3.43 (s, 2H); 4.00 (s, 2H); 7.03-7.05 (d, 2H, J = 8.2 Hz); 7 |
| 10 | 2-[1-(4-Butylphenyl)-2-oxo-1,3-diazaspiro[4.4]non-3-yl]-N-(2,6-diisopropylphenyl)-acetamide | 4-Butyl-phenylamine | cyclopentanone | 100 | DMSO: 0.87-0.91 (t, 3H); 1.10 (s, 6H); 1.12 (s, 6H); 1.28-1.33 (m, 2H); 1.45-1.47 (m, 4H); 1.51-1.57 (m, 2H); 1.66-1.69 (m, 4H); 2.55-2.59 (m, 2H); 3.00-3.07 (m, 2H); 3.33 (s, 2H); 4.00 (s, 2H); 7.06-7.08 (d, 2H, J = 7.3 Hz); 7.14-7.15 (d, 2H, J = 7 |
| 11 | N-(2,6-Diisopropylphenyl)-2-[1-(4-ethylphenyl)-2-oxo-1,3-diazaspiro[4.4]non-3-yl]-acetamide | 4-Ethyl-phenylamine | cyclopentanone | 93 | DMSO: 1.11 (s, 6H); 1.12 (s, 6H); 1.17-1.21 (t, 3H); 1.43-1.50 (m, 4H); 1.62-1.73 (m, 4H); 2.58-2.64 (m, 2H); 3.01-3.07 (m, 2H); 3.41 (s, 2H, 4.01 (s, 2H); 7.07-7.10 (d, 2H, J = 8.23 Hz); 7.14-7.16 (d, 2H, J = 7.76 Hz); 7.23-7.27 (m, 3H); 9.34 (s, |
| 12 | 2-[1-(4-Butylphenyl)-2-oxo-1,3-diazaspiro[4.5]dec-3-yl]-N-(2,6-diisopropylphenyl)-acetamide | 4-Butyl-phenylamine | cyclohexanone | 156 | DMSO: 0.86 (m, 1H); 0.88-0.92 (t, 3H); 1.11 (s, 6H); 1.12 (s, 6H); 1.24-1.35 (m, 6H); 1.47-1.61 (m, 5H); 1.80-1.83 (m, 2H); 2.56-2.60 (m, 2H); 3.01-3.08 (m, 2H); 3.43 (s, 2H); 4.00 (s, 2H); 7.02-7.04 (d, 2H, J = 8.11 Hz); 7.14-7.16 (d, 2H, J = 7.8 H |

| Ex. No. | IUPAC Name | Starting Product 1 | Starting Product 2 | M.p ° C. | NMR |
|---|---|---|---|---|---|
| 13 | 2-(4,4-Diethyl-2-oxo-3-p-tolylimidazolidin-1-yl)-N-(2,6-diisopropylphenyl)acetamide | p-Tolyamine | Pentan-3-one | 120 | DMSO: 0.90-0.94 (t, 6H); 1.17 (s, 6H); 1.18 (s, 6H); 1.48-1.63 (m, 4H); 2.34 (s, 3H); 3.08-3.14 (m, 2H); 3.43 (s, 2H); 4.10 (s, 2H); 7.13-7.15 (d, 2H, J = 8.08 Hz); 7.20-7.22 (m, 2H); 7.29-7.33 (m, 3H); 9.43 (s, 1H) |
| 14 | 2-[1-(4-Benzyloxyphenyl)-2-oxo-1,3-diazaspiro[4.4]non-3-yl]-N-(2,6-diisopropyl-phenyl)acetamide | 4-Benzylozy-phenylamine | cyclopentanone | 176 | DMSO: 1.14 (s, 6H); 1.15 (s, 6H); 1.50-1.54 (m, 4H); 1.70-1.75 (m, 4H); 3.09-3.12 (m, 2H); 3.46 (s, 2H); 4.07 (s, 2H); 5.16 (s, 2H); 7.08-7.10 (d, 2H, J = 7.94 Hz); 7.15-7.17 (d, 2H, J = 7.88 Hz); 7.21-7.23 (d, 2H, J = 7.88 Hz); 7.30-7.32 (m, 2H); 7.3 |
| 15 | 2-[1-(4-Benzyloxyphenyl)-2-oxo-1,3-diazaspiro[4.5]dec-3-yl]-N-(2,6-diisopropyl-phenyl)acetamide | 4-Benzyloxy-phenylamine | cyclohexanone | 194 | DMSO: 0.91-0.97 (m, 1H); 1.19 (s, 6H); 1.20 (s, 6H); 1.24-1.36 (m, 4H); 1.55-1.59 (m, 1H); 1.69 (m, 2H); 1.88-1.90 (m, 2H); 3.09-3.15 (m, 2H); 3.50 (s, 2H); 4.07 (s, 2H); 5.18 (s, 2H); 7.08-7.12 (m, 4H); 7.22-7.24 (d, 2H, J = 7.9 Hz); 7.32-7.33 (m, |

Example 7

N-(2,6-Diisopropylphenyl)-2-(3-oxo-1-phenyl-1,4-diazaspiro[5.5]undec-4-yl)-acetamide, compound (I.7) with R=H; $R_1=R_2=iPr$; $R_3-R_6=-C(O)-CH_2-$; $R_4$ and $R'_4$ are bonded to one another to form a cyclohexyl; $R_5=Ph$

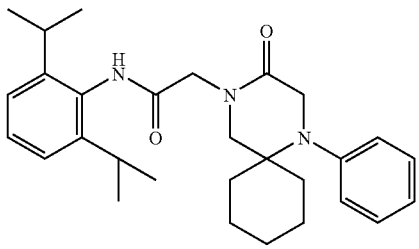

(I.7)

(a) Preparation of Ethyl [(1-phenylaminocyclohexylmethyl)amino]acetate 150 mg (3.75 mmol) of sodium hydride are added to a solution of 700 mg (3.42 mmol) of (1-aminomethylcyclohexyl)phenylamine (obtained in Example 2/b) in 20 ml of dimethylformamide. The solution is stirred for 1 h at room temperature and then 310 µl (3.4 mmol) of ethyl bromoacetate are added. The reaction medium is stirred at room temperature for 2 h and then poured into water and extracted with ethyl acetate. The organic phases are collected and washed with water. They are dried over sodium sulfate. The solvents are evaporated. The residue is chromatographed on silica gel (heptane then heptane/ethyl acetate 80/20, v/v). 652 mg of ethyl [(1-phenylaminocyclohexylmethyl)amino]acetate are obtained in the form of a colorless oil. Yield=65%.

(b) Preparation of Ethyl (3-oxo-1-phenyl-1,4-diazaspiro[5.5]undec-4-yl)acetate 95 mg (0.69 mmol) of potassium carbonate are added to a solution of 200 mg (0.69 mmol) of ethyl [(1-phenylaminocyclohexylmethyl)amino]-acetate and 55 µl (0.69 mmol) of chloroacetyl chloride in 15 ml of dimethylformamide. The reaction medium is stirred at reflux for 6 h and poured into water and extracted with ethyl acetate. The organic phases are collected and washed with water. They are dried over sodium sulfate. The solvents are evaporated. 220 mg of ethyl (3-oxo-1-phenyl-1,4-diazaspiro[5.5]undec-4-yl)acetate are obtained in the form of an orange oil. Yield=97%.

(c) Preparation of (3-Oxo-1-phenyl-1,4-diazaspiro [5.5]undec-4-yl)acetic acid In an analogous manner to Example 2(e), by reaction of 220 mg (0.66 mmol) of ethyl (3-oxo-1-phenyl-1,4-diazaspiro [5.5]undec-4-yl)acetate with 130 mg (3.25 mmol) of sodium hydroxide in 10 ml of tetrahydrofuran, 180 mg of (3-oxo-1-phenyl-1,4-diazaspiro[5.5]undecyl)acetic acid are obtained in the form of a beige solid. M.p. 167-9° C., yield=89%.

(d) Preparation of N-(2,6-Diisopropylphenyl)-2-(3-oxo-1-phenyl-1,4-diazaspiro[5.5]undec-4-yl)acetamide In an analogous manner to Example 2(f), by reaction of 170 mg (0.56 mmol) of (3-oxo-1-phenyl-1,4-diazaspiro[5.5]undec-4-yl)acetic acid with 110 µl (0.58 mmol) of 2,6-diisopropylaniline and 110 mg (0.57 mmol) of 1-(3-dimethylaminopropyl)-3-ethylcarbodiimide in 20 ml of dichloromethane, 130 mg of N-(2,6-diisopropylphenyl)-2-(3-oxo-1-phenyl-1,4-diazaspiro-[5.5]undec-4-yl)acetamide are obtained in the form of a white solid. M.p. 158-60° C., yield=50%.

¹H NMR (CDCl₃; 400 Mz): 1.23 (s, 6H); 1.24 (s, 6H); 1.34-1.46 (m, 6H); 1.70-1.81 (m, 4H); 3.05-3.12 (m, 2H); 3.63 (s, 2H); 3.97 (s, 2H); 4.27 (s, 2H); 7.16-7.24 (m, 4H); 7.29-7.36 (m, 4H); 8.18 (s, 1H).

Example 8 tert-Butyl [(2,6-diisopropylphenylcarbamoyl)methyl]-(1-phenylaminocyclo-hexylmethyl)carbamate, compound (I.8) with R=H; R₁=R₂=iPr; R₃=C(O)R₇; R₄ and R'₄ are bonded to one another to form a cyclohexyl; R₅=Ph, R₆=H, R₇=O^tBu

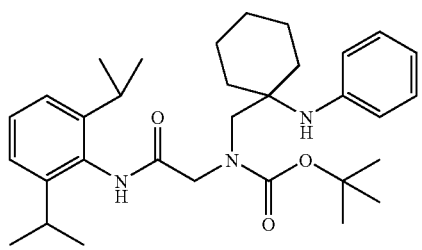

(I.8)

(a) Preparation of N-(2,6-Diisopropylphenyl)-2-[(1-phenylaminocyclohexylmethyl)amino]-acetamide 580 mg (1.94 mmol) of 2-bromo-N-(2,6-diisopropylphenyl)acetamide are added to 400 mg (1.96 mmol) of (1-aminomethylcyclohexyl)phenylamine (obtained in Example 2/b) in 20 ml of dimethylformamide. The reaction medium is stirred at room temperature for 48 h. It is then poured into water and extracted with ethyl acetate. The organic phases are collected and washed with water. They are dried over sodium sulfate. The solvents are evaporated. The residue is chromatographed on silica gel (heptane/ethyl acetate 60/40, v/v). 309 mg of N-(2,6-diisopropylphenyl)-2-[(1-phenylamino-cyclohexylmethyl)amino]acetamide are obtained in the form of a yellowish oil. Yield=37%.

(b) Preparation of tert-Butyl [(2,6-diisopropylphenyl-carbamoyl)methyl]-(1-phenylamino-cyclohexylmethyl)carbamate 155 mg (0.71 mmol) of di-tert-butyl dicarbonate are added to a solution of 300 mg (0.71 mmol) of N-(2,6-diisopropylphenyl)-2-[(1-phenylaminocyclo-hexylmethyl)amino]acetamide in 10 ml of dichloromethane. The reaction medium is stirred at 100° C. for 30 min with microwaves. 98 mg of tert-butyl [(2,6-diisopropylphenylcarbamoyl)methyl]-(1-phenylaminocyclohexyl-methyl)carbamate are obtained in the form of a white solid. M.p. 125-7° C., yield=26%. HPLC 89.4%; Mass: 522.

Example 16

Biological Tests

The compounds of formula (I) according to the invention were subjected to a test allowing their inhibitory action to be evaluated with respect to the enzyme ACAT-1 inspired by the following publication: "Identification of ACAT1- and ACAT2-specific inhibitors using a novel, cell-based fluorescence assay: individual ACAT uniqueness", J. Lipid. Res (2004) vol 45, pages 378-386. The principle of this test is based on the employment of NBD-cholesterol, an analogue of cholesterol whose fluorescence depends on its environment. When this is present in a polar environment, it is weakly fluorescent although in a nonpolar environment it is strongly fluorescent. Free NBD-cholesterol locates itself in the cell membranes and is weakly fluorescent in this polar environment. When the NBD-cholesterol is esterified by ACAT, the ester of NBD-cholesterol locates itself in the nonpolar lipid droplets and is in that case strongly fluorescent.

The method below is applied: The HepG2 cells are incubated in the presence of NBD-cholesterol (1 μg/ml) and of the compound of formula (I) to be tested in black 96-well plates with a transparent base at a rate of 30 000 cells per well. After incubation for 6 h at 37° C., under 5% CO₂, the medium is eliminated by turning over and the cells are washed with 2 times 100 μl of PBS. After addition of 50 μl of lysis buffer (NaPO₄ 10 mM, Igepal 1%), the plates are stirred for 5 min and read in fluorescence (excitation 490 nm, emission 540 nm) on a FUSION apparatus (Perkin-Elmer). By way of illustration, an IC₅₀ of 5.4 nM is obtained for the compound (I.1), an IC₅₀ of 3.2 nM is obtained for the compound (I.5), an IC₅₀ of 7.1 nM is obtained for the compound (I.9) and an IC₅₀ of 0.9 nM is obtained for the compound (I.13).

Example 17

Formulations

Various specific formulations based on compounds according to the invention are given below.

A—Oral Route:
(a) 0.2 g tablet:

| | |
|---|---|
| Compound (I.3) | 0.01 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

(b) Drinkable Suspension in 5 ml Ampoules:

| | |
|---|---|
| Compound (I.1) | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavor | qs |
| Purified water | qsp 5 ml |

B—Topical Route:
(a) Ointment:

| | |
|---|---|
| Compound (I.2) | 0.300 g |
| White petroleum jelly codex | qsp 100 g |

(d) Lotion:

| | |
|---|---|
| Compound (I.4) | 0.100 g |
| Polyethylene glycol (PEG 400) | 69.900 g |
| 95% ethanol | 30.000 g |

(e) Hydrophobic Ointment:

| | |
|---|---|
| Compound (I.1) | 0.300 g |
| Isopropyl myristate | 36.400 g |
| Silicone oil ("Rhodorsil 47 V 300") | 36.400 g |
| Beeswax | 13.600 g |
| Silicone oil ("Abil 300.000 cst") | qsp 100 g |

(f) Nonionic Oil-in-Water Cream:

| | |
|---|---|
| Compound (I.2) | 1.000 g |
| Cetyl alcohol | 4.000 g |
| Glycerol monostearate | 2.500 g |
| PEG 50 stearate | 2.500 g |
| Shea butter | 9.200 g |
| Propylene glycol | 2.000 g |
| Methyl parahydroxybenzoate | 0.075 g |
| Propyl parahydroxybenzoate | 0.075 g |
| Sterile demineralized water | qsp 100 g |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An N-phenylacetamide compound having formula (I):

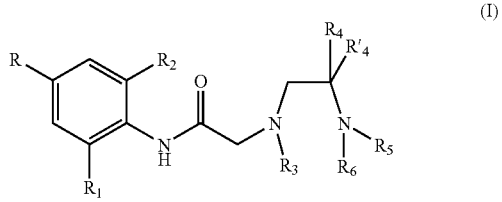

in which:
R is a hydrogen atom, a $(C_1-C_6)$alkyl radical, a —$CH_2$—$NR_aR_b$ radical, a —C(O)—$NR_aR_b$ radical, or a —C(S)—$NR_aR_b$ radical, wherein $R_a$ is a hydrogen atom, or a $(C_1-C_4)$alkyl radical, and $R_b$ is a hydrogen atom, a phenyl, or a cycloalkyl radical;
$R_1$ is a $(C_1-C_6)$alkyl radical;
$R_2$ is a hydrogen, chlorine, fluorine, or bromine atom, or a $(C_1-C_6)$alkyl radical;
$R_3$ is a hydrogen atom, or a —C(O)$R_7$ radical, wherein $R_7$ is a $(C_1-C_6)$alkyl, or $(C_1-C_6)$alkoxy radical;
or else $R_3$ is bonded to $R_6$, and —$R_3$-$R_6$— is —C(O)—, —C(O)$CH_2$—, —$SO_2$—, or —$CH_2$—;
$R_4$ and $R'_4$ are identical and are each a $(C_1-C_6)$alkyl radical;
or else, $R_4$ and $R'_4$ are bonded to one another and form, together with the carbon atom from which they depend, a cycloalkyl group;
$R_5$ is a group selected from among:
(i) an unsubstituted phenyl radical, or a phenyl radical substituted by one, two, or three identical or different substituents selected from among the atoms fluorine, chlorine, iodine, or bromine, or the radicals $(C_1-C_6)$alkyl, hydroxymethyl, monofluoromethyl, difluoromethyl, trifluoromethyl, hydroxyl, phenyl, 2-pyridyl, 3-pyridyl, 4-pyridyl, $(C_1-C_6)$alkoxy, phenoxy, benzyloxy, monofluoromethoxy, difluoromethoxy, or trifluoromethoxy;
(ii) a $(C_1-C_{12})$alkyl radical, optionally substituted by one or more hydroxyl groups, or one or more fluorine, chlorine, iodine, or bromine atoms;
(iii) a cycloalkyl radical, or a —$(CH_2)_m$-cycloalkyl radical in which m is equal to 1, 2, or 3; or,
(iv) an aralkyl radical —$(CH_2)_n$—Ar with n equal to 1, 2, or 3, and Ar is an unsubstituted phenyl radical, unsubstituted naphthyl, or a phenyl radical substituted by one to three identical or different substituents selected from among the atoms fluorine, chlorine, iodine, or bromine, or the radicals $(C_1-C_6)$alkyl, hydroxymethyl, monofluoromethyl, difluoromethyl, trifluoromethyl, hydroxyl, phenyl, 2-pyridyl, 3-pyridyl, 4-pyridyl, $(C_1-C_6)$alkoxy, phenoxy, benzyloxy, monofluoromethoxy, difluoromethoxy, or trifluoromethoxy;
with the proviso that when $R_3$ is bonded to $R_6$ and —$R_3$-$R_6$— is —C(O)$CH_2$—, then $R_5$ is different from a benzyl radical or a group comprising from 4 to 12 carbon atoms of formula —$CH_2$—CH(OH)—$(CH_2)_p$-alkyl in which p is an integer of from 1 and 9, and the alkyl radical can optionally be substituted by one or more hydroxyl groups, or one or more fluorine, chlorine, iodine, or bromine atoms;
$R_6$ is a hydrogen atom, or else $R_6$ is bonded to $R_3$, and —$R_3$-$R_6$— is —C(O)—, —C(O)$CH_2$—, —$SO_2$—, or —$CH_2$—;
and the pharmaceutically acceptable salts, conformers, and rotamers thereof.

2. An N-phenylacetamide compound as defined by claim 1, wherein
R is a hydrogen atom;
$R_1$ is a $(C_1-C_4)$alkyl radical;
$R_2$ is a hydrogen, fluorine, chlorine, or bromine atom, or a $(C_1-C_4)$alkyl radical;
$R_3$ is a hydrogen atom, or a —C(O)$R_7$ radical, wherein $R_7$ is a $(C_1-C_4)$alkyl or $(C_1-C_4)$alkoxy radical;
or else $R_3$ is bonded to $R_6$, and —$R_3$-$R_6$— is —C(O)—, —C(O)$CH_2$—, —$SO_2$—, or —$CH_2$—;
$R_4$ and $R'_4$ are identical and are each a $(C_1-C_4)$alkyl radical;
or else $R_4$ and $R'_4$ are bonded to one another and together form, with the carbon atom from which they depend, a cycloalkyl group having 5, 6, or 7 carbon atoms;
$R_5$ is a group selected from among:
(i) an unsubstituted phenyl radical or phenyl substituted by one, two, or three identical or different substituents selected from among the atoms fluorine, chlorine, or bromine, or the radicals $(C_1-C_4)$alkyl, trifluoromethyl, hydroxymethyl, monofluoromethoxy, difluoromethoxy, trifluoromethoxy, $(C_1-C_4)$alkoxy, phenoxy, benzyloxy, phenyl, 2-pyridyl, 3-pyridyl, or 4-pyridyl;
(ii) a $(C_2-C_{12})$alkyl radical, optionally substituted by one or more hydroxyl groups or one or more fluorine atoms;
(iii) a cycloalkyl radical, or a —$CH_2$-cycloalkyl radical; or,
(iv) an aralkyl radical —$(CH_2)_n$—Ar in which n is equal to 1, 2, or 3, and Ar is an unsubstituted phenyl radical or phenyl monosubstituted by a $(C_1-C_4)$alkyl, trifluoromethyl, or (C$_1$-C$_4$)alkoxy radical, or a fluorine, chlorine, or bromine atom;
with the proviso that when R$_3$ is bonded to R$_6$ and —R$_3$-R$_6$— is —C(O)CH$_2$—, then R$_5$ is different from a benzyl radical or a radical comprising from 4 to 12 carbon atoms of formula —CH$_2$—CH(OH)—(CH$_2$)$_p$-alkyl in which p is an integer of from 1 and 9, and the alkyl radical can optionally be substituted by one or more hydroxyl groups or one or more fluorine atoms; and,
R$_6$ is a hydrogen atom, or else R$_6$ is bonded to R$_3$, and —R$_3$-R$_6$— is —C(O)—, —C(O)CH$_2$—, —SO$_2$—, or —CH$_2$—.

3. An N-phenylacetamide compound as defined by claim 1, wherein R is a hydrogen atom.

4. An N-phenylacetamide compound as defined by claim 1, wherein R$_1$ is a methyl, ethyl, or isopropyl radical.

5. An N-phenylacetamide compound as defined by claim 1, wherein R$_2$ is an ethyl, isopropyl, or tert-butyl radical.

6. An N-phenylacetamide compound as defined by claim 1, wherein
R$_3$ is a hydrogen atom, or a —C(O)R$_7$ radical, and R$_7$ is a methyl radical, or tert-butoxy radical;
or else R$_3$ is bonded to R$_6$, and —R$_3$-R$_6$— is —C(O)—, —C(O)CH$_2$—, —SO$_2$—, or —CH$_2$—.

7. An N-phenylacetamide compound as defined by claim 1, wherein
R$_4$ and R'$_4$ are identical and are each an ethyl or n-propyl radical;
or else, R$_4$ and R'$_4$ are bonded to one another and form, together with the carbon atom from which they depend, a cyclopentyl or cyclohexyl group.

8. An N-phenylacetamide compound as defined by claim 1, wherein
R$_5$ is a group selected from among:
(i) a phenyl radical or phenyl monosubstituted, optionally in the meta or para position, by a methyl, ethyl, n-butyl, or benzyloxy radical, or by a fluorine atom;
(ii) an n-propyl, n-butyl, n-pentyl, n-hexyl, n-heptyl, n-octyl, n-nonyl, sec-butyl, —(CH$_2$)$_2$—OH, —(CH$_2$)$_3$—OH, or —(CH$_2$)$_4$—OH radical;
(iii) a —CH$_2$-cyclopropyl, —CH$_2$-cyclohexyl, cyclopentyl, cyclohexyl, or cycloheptyl radical; or,
(iv) an aralkyl radical —(CH$_2$)$_n$—Ar with n equal to 1 or 2, and Ar is an unsubstituted phenyl radical, or phenyl monosubstituted, optionally in the para position, by a methyl radical, or a fluorine atom;
with the proviso that when R$_3$ is bonded to R$_6$ and —R$_3$-R$_6$— is —C(O)CH$_2$—, then R$_5$ is a phenyl radical or phenyl monosubstituted, optionally in the meta or para position, by a methyl, ethyl, n-butyl, or benzyloxy radical, or by a fluorine atom.

9. An N-phenylacetamide compound as defined by claim 1, wherein R$_1$ and R$_2$ are identical and are each an isopropyl radical.

10. An N-phenylacetamide compound as defined by claim 1, wherein R$_3$ is bonded to R$_6$, and —R$_3$-R$_6$— is —C(O)—.

11. An N-phenylacetamide compound as defined by claim 1, wherein R$_4$ and R'$_4$ are bonded to one another and form, together with the carbon atom from which they depend, a cyclohexyl group.

12. An N-phenylacetamide compound as defined by claim 1, selected from among the following compounds, pharmaceutically acceptable salts, conformers, or rotamers thereof:
N-(2,6-Diisopropylphenyl)-2-(2-oxo-1-phenyl-1,3-diazaspiro[4.5]dec-3-yl)-acetamide;
N-(2,6-Diisopropylphenyl)-2-(1-phenyl-1,3-diazaspiro[4.5]dec-3-yl)-acetamide;
N-(2,6-Diisopropylphenyl)-2-(2,2-dioxo-1-phenyl-2lambda*6*-thia-1,3-diazaspiro[4.5]dec-3-yl)acetamide;
N-(2,6-Diisopropylphenyl)-2-[(1-phenylaminocyclohexylmethyl)amino]-acetamide;
N-(2,6-Diisopropylphenyl)-2-(2,2-dioxo-1-p-tolyl-2lambda*6*-thia-1,3-diazaspiro[4.5]dec-3-yl)acetamide;
N-(2,6-Diisopropylphenyl)-2-(2-oxo-1-p-tolyl-1,3-diazaspiro[4.5]dec-3-yl)acetamide;
N-(2,6-Diisopropylphenyl)-2-(3-oxo-1-phenyl-1,4-diazaspiro[5.5]undec-4-yl)acetamide;
tert-Butyl [(2,6-diisopropylphenylcarbamoyl)methyl]-(1-phenylamino-cyclohexylmethyl)carbamate;
N-(2,6-Diisopropylphenyl)-2-[1-(4-ethylphenyl)-2-oxo-1,3-diaza-spiro[4.5]dec-3-yl]acetamide;
2-[1-(4-Butylphenyl)-2-oxo-1,3-diazaspiro[4.4]non-3-yl]-N-(2,6-diisopropyl-phenyl)acetamide;
N-(2,6-Diisopropylphenyl)-2-[1-(4-ethylphenyl)-2-oxo-1,3-diaza-spiro[4.4]non-3-yl]acetamide;
2-[1-(4-Butylphenyl)-2-oxo-1,3-diazaspiro[4.5]dec-3-yl]-N-(2,6-diisopropyl-phenyl)acetamide;
2-(4,4-Diethyl-2-oxo-3-p-tolylimidazolidin-1-yl)-N-(2,6-diisopropylphenyl)-acetamide;
2-[1-(4-Benzyloxyphenyl)-2-oxo-1,3-diazaspiro[4.4]non-3-yl]-N-(2,6-diiso-propylphenyl)acetamide;
2-[1-(4-Benzyloxyphenyl)-2-oxo-1,3-diazaspiro[4.5]dec-3-yl]-N-(2,6-diiso-propylphenyl)acetamide;
N-(2,6-Diethylphenyl)-2-(2-oxo-1-p-tolyl-1,3-diazaspiro[4.5]dec-3-yl)-acetamide;
N-(2-tert-Butyl-6-methylphenyl)-2-(2-oxo-1-p-tolyl-1,3-diaza-spiro[4.5]dec-3-yl)acetamide;
N-(2,6-Diisopropylphenyl)-2-(2-oxo-4,4-dipropyl-3-p-tolylimidazolidin-1-yl)-acetamide;
N-(2,6-Diisopropylphenyl)-2-(3-oxo-1-p-tolyl-1,4-diazaspiro[5.5]undec-4-yl)acetamide;
N-(2,6-Diisopropylphenyl)-2-[1-(4-fluorophenyl)-2-oxo-1,3-diaza-spiro[4.5]dec-3-yl]acetamide;
N-(2,6-Diisopropylphenyl)-2-(2-oxo-1-p-tolyl-1,3-diazaspiro[4.4]non-3-yl)-acetamide;
N-(2,6-Diisopropylphenyl)-2-[1-(4-fluorophenyl)-2-oxo-1,3-diaza-spiro[4.4]non-3-yl]acetamide;
N-(2,6-Diisopropylphenyl)-2-(2-oxo-1-m-tolyl-1,3-diazaspiro[4.5]dec-3-yl)-acetamide;
N-(2,6-Diisopropylphenyl)-2-(2-oxo-1-propyl-1,3-diazaspiro[4.5]dec-3-yl)-acetamide;
2-(1-Butyl-2-oxo-1,3-diazaspiro[4.5]dec-3-yl)-N-(2,6-diisopropylphenyl)-acetamide;
N-(2,6-Diisopropylphenyl)-2-(2-oxo-1-pentyl-1,3-diazaspiro[4.5]dec-3-yl)-acetamide;
N-(2,6-Diisopropylphenyl)-2-(1-hexyl-2-oxo-1,3-diazaspiro[4.5]dec-3-yl)-acetamide;
N-(2,6-Diisopropylphenyl)-2-(1-heptyl-2-oxo-1,3-diazaspiro[4.5]dec-3-yl)-acetamide;
N-(2,6-Diisopropylphenyl)-2-(1-octyl-2-oxo-1,3-diazaspiro[4.5]dec-3-yl)-acetamide;
N-(2,6-Diisopropylphenyl)-2-(1-nonyl-2-oxo-1,3-diazaspiro[4.5]dec-3-yl)-acetamide;
N-(2,6-Diisopropylphenyl)-2-(1-isobutyl-2-oxo-1,3-diazaspiro[4.5]dec-3-yl)-acetamide;
2-(1-Cyclopropylmethyl-2-oxo-1,3-diazaspiro[4.5]dec-3-yl)-N-(2,6-diiso-propylphenyl)acetamide;
2-(1-Cyclohexylmethyl-2-oxo-1,3-diazaspiro[4.5]dec-3-yl)-N-(2,6-diiso-propylphenyl)acetamide;

2-(1-Cyclopentyl-2-oxo-1,3-diazaspiro[4.5]dec-3-yl)-N-(2,6-diisopropyl-phenyl)acetamide;

2-(1-Cyclohexyl-2-oxo-1,3-diazaspiro[4.5]dec-3-yl)-N-(2,6-diisopropyl-phenyl)acetamide;

2-(1-Cycloheptyl-2-oxo-1,3-diazaspiro[4.5]dec-3-yl)-N-(2,6-diisopropyl-phenyl)acetamide;

2-[Acetyl(1-phenylaminocyclohexylmethyl)amino]-N-(2,6-diisopropyl-phenyl)acetamide;

N-(2,6-Diisopropylphenyl)-2-(2-oxo-1-phenethyl-1,3-diazaspiro[4.5]dec-3-yl)acetamide;

2-(1-Benzyl-2-oxo-1,3-diazaspiro[4.5]dec-3-yl)-N-(2,6-diisopropylphenyl)-acetamide;

N-(2,6-Diisopropylphenyl)-2-[1-(4-methylbenzyl)-2-oxo-1,3-diaza-spiro[4.5]dec-3-yl]acetamide;

N-(2,6-Diisopropylphenyl)-2-[1-(4-fluorobenzyl)-2-oxo-1,3-diaza-spiro[4.5]dec-3-yl]acetamide;

N-(2,6-Diisopropylphenyl)-2-(2-oxo-1-(3-hydroxy)propyl-1,3-diaza-spiro[4.5]dec-3-yl)acetamide;

N-(2,6-Diisopropylphenyl)-2-(2-oxo-1-(4-hydroxy)butyl-1,3-diaza-spiro[4.5]dec-3-yl)acetamide; or, N-(2,6-Diisopropylphenyl)-2-(2-oxo-1-(2-hydroxy)ethyl-1,3-diaza-spiro[4.5]dec-3-yl)acetamide.

13. A medicament comprising at least one N-phenylacetamide compound as defined by claim 1, or a salt, conformer, or rotamer thereof.

14. A pharmaceutical composition comprising at least one N-phenylacetamide compound as defined by claim 1, or a salt, conformer, or rotamer thereof and a physiologically acceptable carrier.

15. A pharmaceutical composition as defined by claim 14, comprising a concentration of compound(s) of formula (I) ranging from 0.001 to 10% by weight relative to the total weight thereof.

16. A pharmaceutical composition as defined by claim 15, comprising a concentration of compound(s) of formula (I) ranging from 0.01 to 2% by weight relative to the total weight thereof.

17. A cosmetic composition comprising at least one N-phenylacetamide compound as defined by claim 1, or a salt, conformer, or rotamer thereof and a physiologically acceptable carrier.

18. A cosmetic composition as defined by claim 17, comprising a concentration of compound(s) of formula (I) ranging from 0.001 to 3% by weight relative to the total weight thereof.

19. A pharmaceutical composition as defined by claim 14, formulated for topical application.

20. A pharmaceutical composition as defined by claim 19, comprising a cream, a milk, a lotion, a gel, an ointment, a pomade, suspensions of microspheres or nanospheres or lipid or polymeric vesicles, impregnated swabs, solutions, sprays, foams, sticks, soaps, shampoos, or washing bases.

21. A cosmetic composition as defined by claim 17, formulated for body or hair hygiene.

22. A method of inhibiting esterification of cholesterol in a subject comprising administering the pharmaceutical composition according to claim 14, to a subject in need thereof.

23. A method of inhibiting SOAT-1 activity in a cell comprising contacting the cell with the pharmaceutical composition according to claim 14.

24. The method according to claim 23, wherein the cell is in a subject in need of SOAT-1 activity being inhibited.

25. A method according to claim 24, wherein the SOAT-1 activity being inhibited is esterification of cholesterol.

* * * * *